United States Patent
Coates et al.

(10) Patent No.: US 11,746,115 B2
(45) Date of Patent: Sep. 5, 2023

(54) SOLID FORMS OF 7-[[(1S)-1-[4-[(1S)-2-CY-CLOPROPYL- 1-(4-PROP-2- ENOYLPIPE-RAZIN-1-YL)ETHYL]PHENYL]ETHYL]A-MINO]-1-ETHYL-4H-PYRIMIDO[4,5-D][1,3]OXAZIN-2-ONE

(71) Applicant: Eli Lilly and Company, Indianapolis, IN (US)

(72) Inventors: David Andrew Coates, New Palestine, IN (US); Yizheng Cao, West Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/886,863

(22) Filed: Aug. 12, 2022

(65) Prior Publication Data

US 2023/0061806 A1   Mar. 2, 2023

Related U.S. Application Data

(60) Provisional application No. 63/310,692, filed on Feb. 16, 2022, provisional application No. 63/290,403, filed on Dec. 16, 2021, provisional application No. 63/232,846, filed on Aug. 13, 2021.

(51) Int. Cl.
*C07D 498/04* (2006.01)
*A61P 35/00* (2006.01)
*C07C 65/05* (2006.01)

(52) U.S. Cl.
CPC ........ *C07D 498/04* (2013.01); *C07B 2200/13* (2013.01)

(58) Field of Classification Search
CPC ... C07D 498/04; C07B 2200/13; A61P 35/00; C07C 65/05
See application file for complete search history.

(56) References Cited

FOREIGN PATENT DOCUMENTS

| WO | 2013/046136 A1 | 4/2013 |
|---|---|---|
| WO | 2016/171755 A1 | 10/2016 |
| WO | 2017/019429 A1 | 2/2017 |
| WO | 2017/213910 A1 | 12/2017 |
| WO | 2018/111707 A1 | 6/2018 |
| WO | 2021/194946 A1 | 9/2021 |
| WO | 2021/194950 A1 | 9/2021 |
| WO | 2021/194953 A1 | 9/2021 |
| WO | 2022/020281 A1 | 1/2022 |

OTHER PUBLICATIONS

Paschka, P., et al., "IDH1 and IDH2 Mutations are Frequent Genetic Alterations in Acute Myeloid Leukemia and Confer Adverse Prognosis in Cytogenetically Normal Acute Myeloid Leukemia With NPM1 Mutation Without FLT3 Internal Tandem Duplication," J. Clin. Oncol. 2010; 28: 3636-3643.

Stephen Byrn et al: "Pharmaceutical Solids: A Strategic Approach to Regulatory Considerations", Pharmaceutical Research, 12 (7), 1995, pp. 945-954.

Mino R Caira Ed.—Montchamp J.-L.: "Crystalline Polymorphism of Organic Compounds", Topics in Current Chemistry, 198, 1998, pp. 163-208.

Serajuddin et at.: "Salt formation to improve drug solubility", Advanced Drug Delivery Reviews, 59 (7), 2007, pp. 603-616.

Heinrich Stahl P Ed—Wermuth C G: "The Practice of Medicinal Chemistry; 35 Preparation of water-soluble compounds through salt formation", 2003, The Practice of Medicinal Chemistry, pp. 601-615.

Written Opinion for PCT/US2022/040191 (dated Oct. 12, 2022).
International Search Report for PCT/US2022/040191 (dated Oct. 12, 2022).

*Primary Examiner* — John M Mauro
(74) *Attorney, Agent, or Firm* — Joseph M Pletcher

(57) ABSTRACT

Solid forms including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and a dihydroxybenzoic acid selected from 2,5-dihydroxybenzoic acid, 2,4-dihydroxybenzoic acid, and 2,3-dihydroxybenzoic acid are provided, as well as pharmaceutical compositions including the solid forms, methods for using the solid forms in treating cancer patients, and methods of making the solid forms.

25 Claims, 9 Drawing Sheets

SOLID FORMS OF 7-[[(1S)-1-[4-[(1S)-2-CYCLOPROPYL-1-(4-PROP-2-ENOYLPIPERAZIN-1-YL)ETHYL]PHENYL]ETHYL]AMINO]-1-ETHYL-4H-PYRIMIDO[4,5-D][1,3]OXAZIN-2-ONE

IDH1 and IDH2 are enzymes that catalyze the conversion of isocitrate to α-ketoglutarate and reduce nicotinamide adenine dinucleotide phosphate (NADP$^+$) to NADPH (Megias-Vericat J, et al., *Blood Lymph. Cancer: Targets and Therapy* 2019; 9: 19-32).

Neomorphic (de novo) mutations in IDH1, e.g., at IDH1 amino acid residue R132, contribute to tumorigenesis in several types of cancer, including solid tumor cancers and hematologic malignancies (Badur M G, et al., *Cell Reports* 2018; 25: 1680). IDH1 mutations can result in high levels of 2-hydroxyglutarate (2-HG), which inhibits cellular differentiation, and inhibitors of mutant IDH1 can reduce 2-HG levels, which promotes cellular differentiation (Molenaar R J, et al., *Oncogene* 2018; 37: 1949-1960). Mutations also occur in IDH2, e.g., at amino acid residues R140 and R172 (Yang H, et al., *Clin. Cancer. Res.* 2012; 18: 5562-5571; Mondesir J, et al., *J. Blood Med.* 2016; 7: 171-180).

Certain mutant IDH1 and IDH2 inhibitors are disclosed in WO 2018/111707 A1, including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one ("Compound A"), which is the compound of the structure:

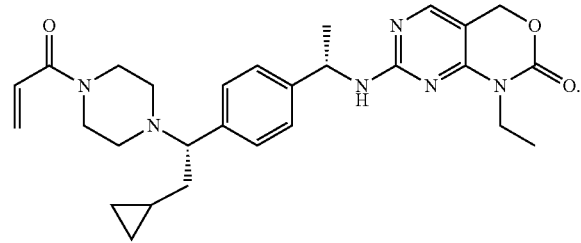 [SMILES: C=CC(=O)N1CCN([C@@H](CC2CC2)c2ccc([C@H](C)Nc3ncc4c(n3)N(CC)C(=O)OC4)cc2)CC1]

Compound A is currently in phase 1 studies for advanced hematologic malignancies (NCT04603001) and advanced solid tumors (NCT04521686). Certain preclinical studies determined that Compound A is more soluble in an acidic environment than a neutral one, and that drug absorption may be adversely impacted by elevated stomach pH. Consequently, the phase 1 studies place certain restrictions on patient food intake and use of gastric acid reducing agents. The studies limit food intake to at least 2 hours before and for at least 1 hour after the dose of Compound A. Where concurrent use of an H2 blocker or antacid is necessary, it must be administered at least 2 hours before or after the dose of Compound A. Further, concomitant use of proton pump inhibitors (PPIs) is prohibited due to their long pharmacodynamic half-life, and patients must discontinue PPIs one or more weeks prior to the first dose of Compound A. Thus, there exists a need for physically and chemically stable solid forms of Compound A that provide consistent exposure across the patient population, and provide more flexible dosing, such as concurrent food consumption or concurrent use of gastric acid reducing agents (e.g., H2 blockers, antacids, or PPIs).

Figure 1:
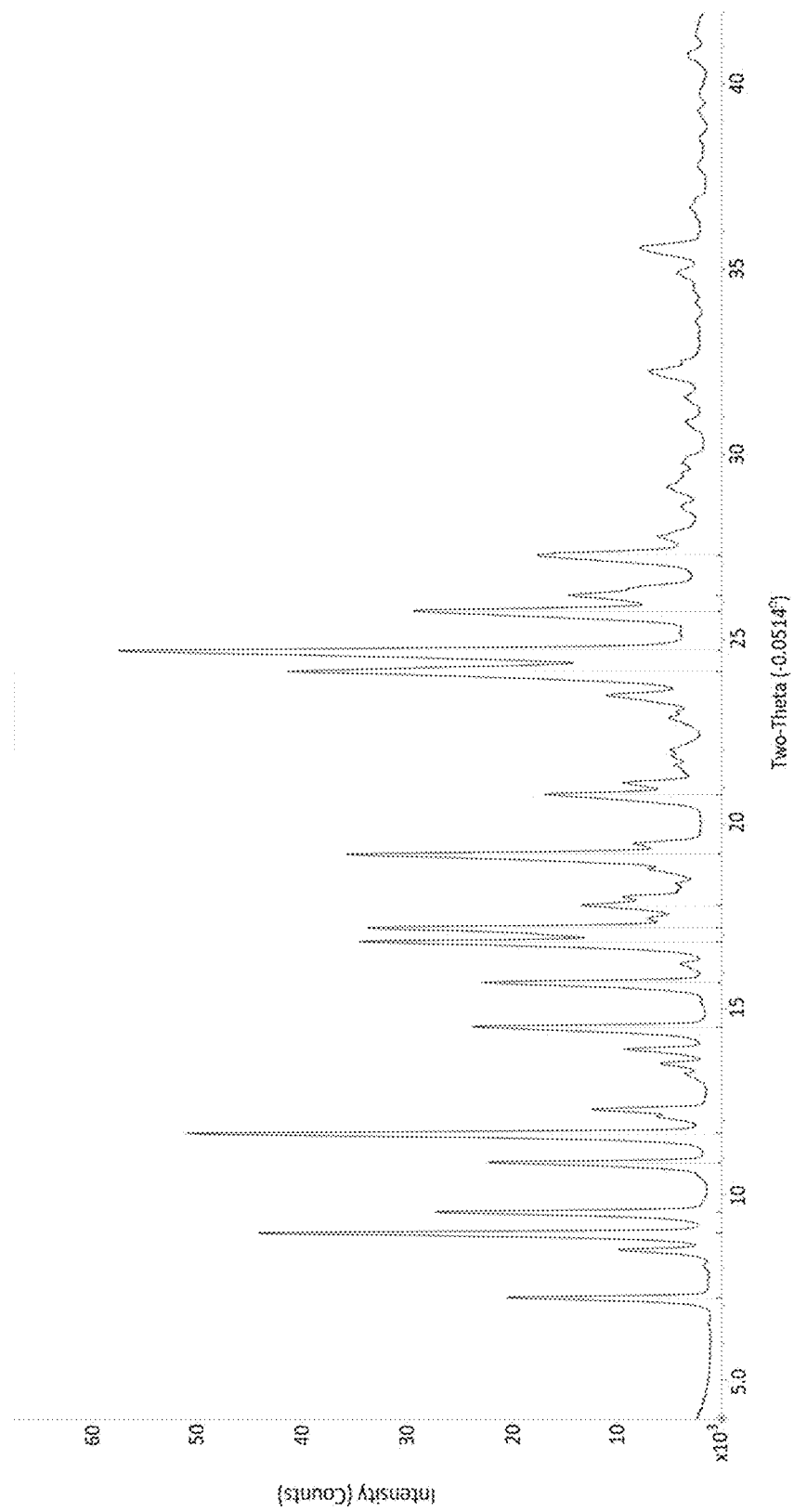
FIG. 1 is an XRPD pattern of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

The present invention provides physically and chemically stable solid forms of Compound A having advantageous solubility and pharmacokinetic properties. The solid forms may provide consistent exposure across the patient population, and more flexible dosing, such as concurrent food consumption or concurrent use of gastric acid reducing agents (e.g., H2 blockers, antacids, or PPIs).

The solid forms include 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and a dihydroxybenzoic acid selected from 2,5-dihydroxybenzoic acid, 2,4-dihydroxybenzoic acid, and 2,3-dihydroxybenzoic acid. In an embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the dihydroxybenzoic acid are in a molar ratio of about 1:2. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the dihydroxybenzoic acid are in a molar ratio of 1:2.

In one aspect, the solid form includes 7-[[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,5-dihydroxybenzoic acid. In an embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,5-dihydroxybenzoic acid are in a molar ratio of about 1:2. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,5-dihydroxybenzoic acid are in a molar ratio of 1:2, referred to herein as 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), or 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one, bis(2,5-dihydroxybenzoate), which can be represented by the structure:

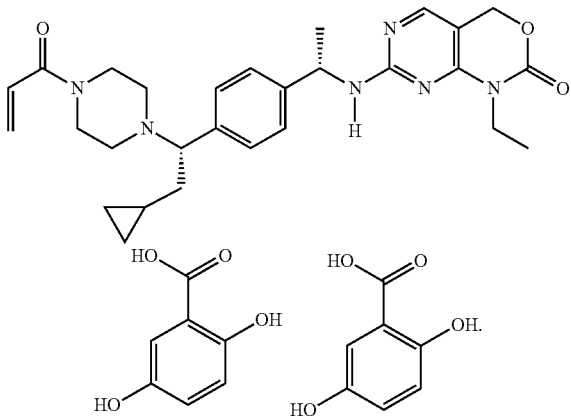

In another embodiment, the solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,5-dihydroxybenzoic acid is a crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,5-dihydroxybenzoic acid are in a molar ratio of about 1:2 in the crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,5-dihydroxybenzoic acid are in a molar ratio of 1:2 in the crystalline solid, referred to herein as crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,5-dihydroxybenzoate).

In another embodiment, the solid form is an anhydrous non-solvated crystalline solid referred to herein as crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I, or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,5-dihydroxybenzoate) Form I, or Compound A digentisate Form I.

In an embodiment, Form I is characterized by an X-ray powder diffraction pattern using CuKa radiation having a peak at diffraction angle 2-theta of 9.0°±0.2° in combination with at least one peak selected from 7.2°±0.2°, 9.5°±0.2°, 10.9°±0.2°, 11.7°±0.2°, 14.5°±0.2°, 15.7°±0.2°, 16.8°±0.2°, 17.2°±0.2°, 19.2°±0.2°, 20.8°±0.2°, 24.1°±0.2°, 24.7°±0.2°, and 25.8°±0.2°. In another embodiment, Form I is characterized by an X-ray powder diffraction pattern using CuKa radiation having a peak at diffraction angle 2-theta of 9.0°±0.2° in combination with at least one peak selected from 7.2°±0.2°, 9.5°±0.2°, and 11.7°±0.2°.

In another embodiment, Form I is characterized by a $^{13}C$ solid state NMR (100.6 MHz) spectrum which comprises at least one peak referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, or 175.2 ppm (±0.2 ppm, respectively). In another embodiment, Form I is characterized by a $^{13}C$ solid state NMR (100.6 MHz) spectrum which comprises at least one peak referenced to the high-field resonance of adamantane (d=29.5 ppm) at: 12.8, 23.9, 41.9, 68.1, 149.4, or 155.1 ppm (±0.2 ppm, respectively). In another embodiment, Form I is characterized by a $^{13}C$ solid state NMR (100.6 MHz) spectrum which comprises peaks referenced to the high-field resonance of adamantane (d=29.5 ppm) at: 12.8, 23.9, 41.9, 68.1, 149.4, and 155.1 ppm (±0.2 ppm, respectively).

In another embodiment, the solid form is a crystalline solid isostructural solvate referred to herein as crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II, or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,5-dihydroxybenzoate) Form II. In an embodiment, Form II is an isostructural solvate of acetone or methyl ethyl ketone (MEK). In another embodiment, Form II is an acetone solvate. In another embodiment, Form II is an MEK solvate. In an embodiment, Form II is characterized by an X-ray powder diffraction pattern using CuKa radiation having a peak at diffraction angle 2-theta of 6.5°±0.2° in combination with at least one peak selected from 4.9°±0.2°, 7.5°±0.2°, 8.2°±0.2°, 9.9°±0.2°, 12.0°±0.2°, 12.7°±0.2°, 14.8°±0.2°, 15.0°±0.2°, 15.4°±0.2°, 16.0°±0.2°, 17.0°±0.2°, 17.4°±0.2°, and 19.6°±0.2°. In another embodiment, Form II is characterized by an X-ray powder diffraction pattern using CuKa radiation having a peak at diffraction angle 2-theta of 6.5°±0.2° in combination with at least one peak selected from 4.9°±0.2°, 8.2°±0.2°, and 12.7°±0.2°.

In another embodiment, the solid form is an anhydrous non-solvated crystalline solid referred to herein as 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III, or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,5-dihydroxybenzoate) Form III.

In an embodiment, Form III is characterized by an X-ray powder diffraction pattern using CuKa radiation having a peak at diffraction angle 2-theta of 5.5°±0.2° in combination with at least one peak selected from 8.5°±0.2°, 11.0°±0.2°, 11.9°±0.2°, 12.4°±0.2°, 14.0°±0.2°, 14.3°±0.2°, 16.3°±0.2°, 16.6°±0.2°, 17.0°±0.2°, and 19.1°±0.2°. In another embodiment, Form III is characterized by an X-ray powder diffraction pattern using CuKa radiation having a peak at diffraction angle 2-theta of 5.5°±0.2° in combination with at least one peak selected from 8.5°±0.2°, 11.0°±0.2°, and 11.9°±0.2°.

In another embodiment, the solid form is an amorphous solid referred to herein as amorphous 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), or amorphous 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,5-dihydroxybenzoate).

In another aspect, the solid form includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,4-dihydroxybenzoic acid. In an embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,4-dihydroxybenzoic acid are in a molar ratio of about 1:2. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,4-dihydroxybenzoic acid are in a molar ratio of 1:2, referred to herein as 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), or 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,4-dihydroxybenzoate), which can be represented by the structure:

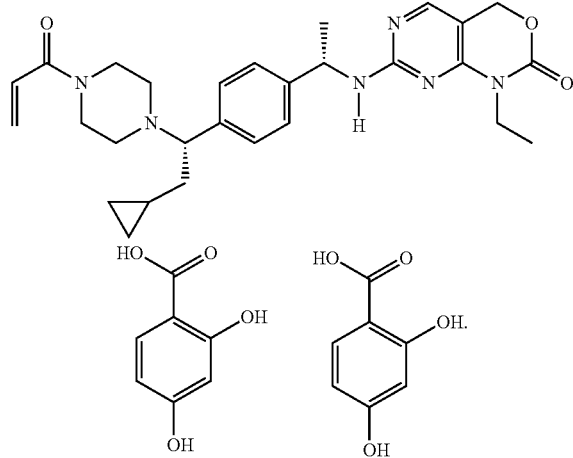

In another embodiment, the solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,4-dihydroxybenzoic acid is a crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,4-dihydroxybenzoic acid are in a molar ratio of about 1:2 in the crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,4-dihydroxybenzoic acid are in a molar ratio of 1:2 in the crystalline solid, referred to herein as crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,4-dihydroxybenzoate).

In another aspect, the solid form includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,3-dihydroxybenzoic acid. In an embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,3-dihydroxybenzoic acid are in a molar ratio of about 1:2. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,3-dihydroxybenzoic acid are in a molar ratio of 1:2, referred to herein as 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), or 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,3-dihydroxybenzoate), which can be represented by the structure:

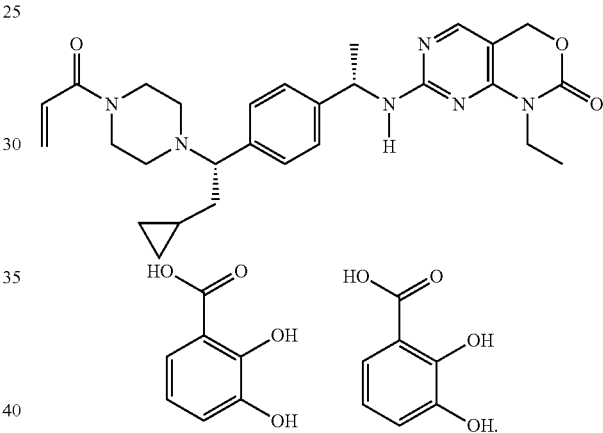

In another embodiment, the solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,3-dihydroxybenzoic acid is a crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,3-dihydroxybenzoic acid are in a molar ratio of about 1:2 in the crystalline solid. In another embodiment, the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the 2,3-dihydroxybenzoic acid are in a molar ratio of 1:2 in the crystalline solid, referred to herein as crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), or crystalline 7-(((S)-1-(4-((S)-1-(4-acryloylpiperazin-1-yl)-2-cyclopropylethyl)phenyl)ethyl)amino)-1-ethyl-1,4-dihydro-2H-pyrimido[4,5-d][1,3]oxazin-2-one bis(2,3-dihydroxybenzoate).

In another embodiment, the solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,3-dihydroxybenzoic acid is a crystalline solid characterized by an X-ray powder diffraction (XRPD)

pattern using CuKa radiation having a peak at diffraction angle 2-theta of 11.5°±0.2° in combination with at least one peak selected from 7.5°±0.2°, 8.9°±0.2°, 9.3°±0.2°, 10.9°±0.2°, 12.3°±0.2°, 14.0°±0.2°, 15.0°±0.2°, 16.6°±0.2°, 17.3°±0.2°, 18.7°±0.2°, 21.1°±0.2°, 23.7°±0.2°, 24.6°±0.2°, and 25.8°±0.2°. In another embodiment, the crystalline solid is characterized by an XRPD pattern using CuKa radiation having a peak at diffraction angle 2-theta of 11.5°±0.2° in combination with at least one peak selected from 8.9°±0.2°, 15.0°±0.2°, and 24.6°±0.2°.

Further provided is a process to prepare a solid form as described herein. The process includes providing a solution including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, a dihydroxybenzoic acid selected from 2,5-dihydroxybenzoic acid, 2,4-dihydroxy benzoic acid, and 2,3-dihydroxybenzoic acid, and a solvent; and precipitating from the solution a solid form, preferably a crystalline solid form, as described herein.

In one aspect, the process includes providing a solution including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid, and a solvent; and precipitating from the solution a solid form, preferably a crystalline solid form, including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,5-dihydroxybenzoic acid, as described herein, preferably crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), more preferably crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I. In an embodiment, the solvent is acetonitrile, ethyl acetate, isopropyl alcohol, or water. In an embodiment, the solvent is acetonitrile. In another embodiment, the solution is heated to above room temperature prior to the precipitation, preferably about 70° C. In another embodiment, at least two equivalents of the 2,5-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile and the solution is heated to above room temperature prior to the precipitation, preferably about 70° C. In another embodiment, the solvent is acetonitrile and at least two equivalents of the 2,5-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solution is heated to above room temperature prior to the precipitation, preferably about 70° C., and at least two equivalents of the 2,5-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile, the solution is heated to above room temperature prior to the precipitation, preferably about 70° C., and at least two equivalents of the 2,5-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

In another aspect, the process includes providing a solution comprising 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid, and a solvent; and precipitating from the solution a solid form, preferably a crystalline solid form, including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,4-dihydroxybenzoic acid, as described herein, preferably crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2). In an embodiment, the solvent is acetonitrile, ethyl acetate, isopropyl alcohol, or water. In an embodiment, the solvent is acetonitrile. In another embodiment, the solution is heated to above room temperature prior to the precipitation, preferably about 70° C. In another embodiment, at least two equivalents of the 2,4-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile and the solution is heated to above room temperature prior to the precipitation, preferably about 70° C. In another embodiment, the solvent is acetonitrile and at least two equivalents of the 2,4-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solution is heated to above room temperature prior to the precipitation, preferably about 70° C., and at least two equivalents of the 2,4-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile, the solution is heated to above room temperature prior to the precipitation, preferably about 70° C., and at least two equivalents of the 2,4-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

In another aspect, the process includes providing a solution comprising 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid, and a solvent; and precipitating from the solution a solid form, preferably a crystalline solid form, including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,3-dihydroxybenzoic acid, as described herein, preferably crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2). In an embodiment, the solvent is acetonitrile, ethyl acetate, isopropyl alcohol, or water. In an embodiment, the solvent is acetonitrile. In another embodiment, the solution is heated to above room temperature prior to the precipitation, preferably about 70° C. In another embodiment, at least two equivalents of the 2,3-dihydroxybenzoic acid are used relative to the 7-[[(1S) [4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile and the solution is heated to above room temperature prior to the precipitation, preferably about 70° C. In another embodiment, the solvent is acetonitrile and at least two equivalents of the 2,3-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solution is heated to above room temperature prior to the precipitation, preferably about 70° C., and at least two equivalents of the 2,3-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. In another embodiment, the solvent is acetonitrile, the solution is heated to above room temperature prior to the precipitation, preferably about 70° C., and at least two equivalents of the 2,3-dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

Further provided is a pharmaceutical composition including a solid form as described herein, and a pharmaceutically acceptable carrier, diluent, or excipient. The solid form can be formulated as a pharmaceutical composition that can be administered by a variety of routes. In an embodiment, such compositions are formulated for oral administration. Pharmaceutical compositions, and processes for preparing the same, are well known in the art (see, e.g., *Remington: The Science and Practice of Pharmacy* (A. Gennaro, et al., eds., 21st ed., Mack Publishing Co., 2005)).

In one aspect, the pharmaceutical composition includes a solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,5-dihydroxybenzoic acid, as described herein, and a pharmaceutically acceptable carrier, diluent, or excipient. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), as described herein, and microcrystalline cellulose, mannitol, polyvinylpyrrolidone vinyl acetate, croscarmellose sodium, colloidal silica dioxide, and sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I, as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I, as described herein, and microcrystalline cellulose, mannitol, polyvinylpyrrolidone vinyl acetate, croscarmellose sodium, colloidal silica dioxide, and sodium stearyl fumarate.

In another aspect, the pharmaceutical composition includes a solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,4-dihydroxybenzoic acid, as described herein, and a pharmaceutically acceptable carrier, diluent, or excipient. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), as described herein, and microcrystalline cellulose, mannitol, polyvinylpyrrolidone vinyl acetate, croscarmellose sodium, colloidal silica dioxide, and sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2), as described herein, and microcrystalline cellulose, mannitol, polyvinylpyrrolidone vinyl acetate, croscarmellose sodium, colloidal silica dioxide, and sodium stearyl fumarate.

In another aspect, the pharmaceutical composition includes a solid form including 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,3-dihydroxybenzoic acid, as described herein, and a pharmaceutically acceptable carrier, diluent, or excipient. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), as described herein, and microcrystalline cellulose, mannitol, polyvinylpyrrolidone vinyl acetate, croscarmellose sodium, colloidal silica dioxide, and sodium stearyl fumarate. In an embodiment, the pharmaceutical composition includes crystalline 7-[[(1S)-1-[4-[(1S)-2-cyclopropyl- 1-(4-prop enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), as described herein, and microcrystalline cellulose, mannitol, polyvinylpyrrolidone vinyl acetate, croscarmellose sodium, colloidal silica dioxide, or sodium stearyl fumarate. In an embodiment, the pharmaceutical composition includes crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), as described herein, and microcrystalline cellulose, mannitol, polyvinylpyrrolidone vinyl acetate, croscarmellose sodium, colloidal silica dioxide, and sodium stearyl fumarate.

Further provided is a combination including a solid form as described herein, and one or more therapeutic agents. The solid form and the one or more other therapeutic agents can be administered as a simultaneous, separate or sequential combination. The solid form and the one or more other therapeutic agents can be administered, for example, as independent pharmaceutical compositions for simultaneous, separate, or sequential administration, or as part of a unitary pharmaceutical composition including a pharmaceutically acceptable carrier, diluent, or excipient.

In one aspect, the combination includes a solid form as described herein, and an antimetabolite agent, a hypomethylating agent, a Bcl-2 inhibitor, a mutant Flt3 inhibitor, or a deoxyadenosine analog and a platinum agent. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In an embodiment, the combination includes a solid form as described herein, and an antimetabolite agent, or a pharmaceutically acceptable salt thereof. In an embodiment, the antimetabolite agent is cytarabine, 5-fluorouracil (5-FU), 6-mercaptourine (6-MP), capecitabine, floxuridine, fludarabine, gemcitabine, hydroxycarbamide, methotrexate, pemetrexed, or phototrexate, or a pharmaceutically acceptable salt of any one of them. In another embodiment, the antimetabolite agent is cytarabine, or a pharmaceutically acceptable salt thereof. In another embodiment, the anti-metabolite agent is cytarabine. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment, the combination includes a solid form as described herein, and a hypomethylating agent, or a pharmaceutically acceptable salt thereof. In another embodiment, the hypomethylating agent is azacitidine (5-azacitidine), 5-aza-2'-deoxycitidine (Decitabine), guadecitabine (SGI-110), 5-fluor-2'-deoxycitidine, zebularine, CP-4200, RG108, or nanaomycin A, or a pharmaceutically acceptable salt of any one of them. In another embodiment, the hypomethylating agent is azacitidine, or a pharmaceutically acceptable salt thereof. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment, the combination includes a solid form as described herein, and a Bcl-2 inhibitor, or a pharmaceutically acceptable salt thereof. In another embodiment, the Bcl-2 inhibitor is venetoclax, obatoclax, or navitoclax, or a pharmaceutically acceptable salt of any one of them. In another embodiment, the Bcl-2 inhibitor is venetoclax, or a pharmaceutically acceptable salt thereof. In another embodiment, the Bcl-2 inhibitor is venetoclax. Preferably, the solid form is 7-[[(1S) [4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment, the combination includes a solid form as described herein, and a hypomethylating agent, or a pharmaceutically acceptable salt thereof, and a Bcl-2 inhibitor, or a pharmaceutically acceptable salt thereof. In another embodiment, the hypomethylating agent is azacitidine and the Bcl-2 inhibitor is venetoclax. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment, the combination includes a solid form as described herein, and a mutant Flt3 inhibitor, or a pharmaceutically acceptable salt thereof. In another embodiment, the mutant Flt3 inhibitor is midostaurin, gilteritinib, quizartinib (AC220), sorafenib, sunitinib, lestaurtinib, or crenolanib, or a pharmaceutically acceptable salt of any one of them. In another embodiment, the mutant Flt3 inhibitor is midostaurin, or a pharmaceutically acceptable salt thereof. In another embodiment, the mutant Flt3 inhibitor is midostaurin. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2- one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-1-4H-pyrimido[4,5-d][1,3]oxazin-2-one, 2,5-dihydroxybenzoic acid (1:2) Form I.

In another embodiment, the combination includes a solid form as described herein, and a deoxyadenosine analog and a platinum agent. In another embodiment, the deoxyadenosine analog is cytarabine or gemcitabine, or a pharmaceutically acceptable salt thereof. In another embodiment, the deoxyadenosine analog is gemcitabine, or a pharmaceutically acceptable salt thereof. In another embodiment, the deoxyadenosine analog is gemcitabine. In another embodiment, the platinum agent is cisplatin, carboplatin or oxaliplatin. In another embodiment, the platinum agent is cisplatin. In another embodiment, the deoxyadenosine analog is gemcitabine and the platinum agent is cisplatin. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Further provided is a method of treating a cancer in a patient expressing an IDH mutation, by administering to a patient in need thereof a therapeutically effective amount of a solid form as described herein. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Further provided is a solid form as described herein, for use in treating a cancer in a patient expressing an IDH mutation. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Further provided is use of a solid form as described herein, for the manufacture of a medicament for the treatment of a cancer in a patient expressing an IDH mutation. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In an embodiment of the method of treatment or the solid form for use, the IDH mutation is an IDH1 mutation or an IDH2 mutation.

In another embodiment of the method of treatment or the solid form for use, the IDH mutation is an IDH1 mutation. In another embodiment of the method of treatment or the solid form for use, the IDH1 mutation is an IDH1 R132 mutation. In another embodiment of the method of treatment or the solid form for use, the IDH1 R132 mutation is R132C, R132G, R132H, R132L, or R132S. In another embodiment of the method of treatment or the solid form for use, the IDH1 R132 mutation is R132C. In another embodiment of the method of treatment or the solid form for use, the IDH1 R132 mutation is R132G. In another embodiment of the method of treatment or the solid form for use, the IDH1 R132 mutation is R132H. In another embodiment of the method of treatment or the solid form for use, the IDH1 R132 mutation is R132L. In another embodiment of the method of treatment or the solid form for use, the IDH1 R132 mutation is R132S.

In another embodiment of the method of treatment or the solid form for use, the IDH mutation is an IDH2 mutation. In another embodiment of the method of treatment or the solid form for use, the IDH2 mutation is an IDH2 R140 mutation or an IDH2 R172 mutation. In another embodiment of the method of treatment or the solid form for use, the IDH2 mutation is an IDH2 R140 mutation. In another embodiment of the method of treatment or the solid form for use, the IDH2 R140 mutation is R140Q, R140L, or R140W. In another embodiment of the method of treatment or the solid form for use, the IDH2 R140 mutation is R140Q. In another embodiment of the method of treatment or the solid form for use, the IDH2 R140 mutation is R140L. In another embodiment of the method of treatment or the solid form for use, the IDH2 R140 mutation is R140W. In another embodiment of the method of treatment or the solid form for use, the IDH2 mutation is an IDH2 R172 mutation. In another embodiment of the method of treatment or the solid form for use, the IDH2 R172 mutation is R172K, R172M, R172G, R172S or R172W. In another embodiment of the method of treatment or the solid form for use, the IDH2 R172 mutation is R172K. In another embodiment of the method of treatment or the solid form for use, the IDH2 R172 mutation is R172M. In another embodiment of the method of treatment or the solid form for use, the IDH2 R172 mutation is R172G. In another embodiment of the method of treatment or the solid form for use, the IDH2 R172 mutation is R172S. In another embodiment of the method of treatment or the solid form for use, the IDH2 R172 mutation is R172W.

In an embodiment of the method of treatment or the solid form for use, the cancer is a solid tumor cancer. In another embodiment of the method of treatment or the solid form for use, the solid tumor cancer is cholangiocarcinoma, head and neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma. In another embodiment of the method of treatment or the solid form for use, the cancer is non-small cell lung cancer.

In another embodiment of the method of treatment or the solid form for use, the solid tumor cancer is cholangiocarcinoma.

In an embodiment of the method of treatment or the solid form for use, the cancer is a hematologic malignancy. In another embodiment of the method of treatment or the solid form for use, the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia. In another embodiment of the method of treatment or the solid form for use, the hematologic malignancy is acute myeloid leukemia.

In an embodiment of the method of treatment or the solid form for use, the cancer is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma, or cholangiocarcinoma.

In another embodiment of the method of treatment or the solid form for use, the patient is identified as having an IDH1 mutation, e.g., an IDH1 R132 mutation. In another embodiment of the method of treatment or the solid form for use, the patient is identified as having an IDH2 mutation, e.g., an IDH2 R140 or R172 mutation.

In another embodiment of the method of treatment or the solid form for use, the patient is identified as having an IDH mutation in blood, bone marrow, lymph node, lymphatic fluid, blood cells, bone marrow cells, lymph node cells or lymphatic fluid cells.

In another embodiment of the method of treatment or the solid form for use, the cancer is a hematologic malignancy, and the patient is identified as having an IDH mutation in blood, bone marrow, lymph node or lymphatic fluid.

In another embodiment of the method of treatment or the solid form for use, the patient is identified as having an IDH mutation in tissue. In another embodiment of the method of treatment or the solid form for use, the patient is identified as having an IDH mutation in solid tumor tissue. In another embodiment of the method of treatment or the solid form for use, the cancer is a solid tumor cancer, and the patient is identified as having an IDH1 mutation in solid tumor tissue.

In another embodiment of the method of treatment or the solid form for use, the cancer is frontline cancer. In another embodiment of the method of treatment or the solid form for use, the frontline cancer is a solid tumor cancer. In another embodiment of the method of treatment or the solid form for use, the frontline cancer is a hematologic malignancy. In another embodiment of the method of treatment or the solid form for use, the frontline hematologic malignancy is frontline AML.

In another embodiment of the method of treatment or the solid form for use, the cancer is relapsed cancer. In another embodiment of the method of treatment or the solid form for use, the relapsed cancer is a solid tumor cancer. In another embodiment of the method of treatment or the solid form for use, the relapsed cancer is a hematologic malignancy. In another embodiment of the method of treatment or the solid form for use, the relapsed hematologic malignancy is relapsed AML.

In another embodiment of the method of treatment or the solid form for use, the cancer is refractory cancer. In another embodiment of the method of treatment or the solid form for use, the refractory cancer is a solid tumor cancer. In another embodiment of the method of treatment or the solid form for use, the refractory cancer is a hematologic malignancy. In another embodiment of the method of treatment or the solid form for use, the refractory hematologic malignancy is refractory AML.

In another embodiment of the method of treatment or the solid form for use, the cancer is advanced cancer. In another embodiment of the method of treatment or the solid form for use, the advanced cancer is an advanced solid tumor cancer. In another embodiment of the method of treatment or the solid form for use, the advanced cancer is an advanced hematologic malignancy. In another embodiment of the method of treatment or the solid form for use, the advanced hematologic malignancy is advanced AML. In another embodiment of the method of treatment or the solid form for use, the AML is acute promyelocytic leukemia.

In another embodiment of the method of treatment or the solid form for use, the solid form is administered with or without food. In another embodiment of the method of treatment or the solid form for use, the solid form is administered with food. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, food is consumed before (e.g., within 2 hours before) administration of the solid form. In another embodiment of the method of treatment or the solid form for use, food is consumed within 2 hours before administration of the solid form. In another embodiment of the method of treatment or the solid form for use, food is consumed within 1 hour before administration of the solid form. In another embodiment of the method of treatment or the solid form for use, food is consumed within 0.5 hour before administration of the solid form. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, food is consumed after (e.g., within 1 hour after) administration of the solid form. In another embodiment of the method of treatment or the solid form for use, food is consumed within 1 hour after administration of the solid form. In another embodiment of the method of treatment or the solid form for use, food is consumed within 0.5 hour after administration of the solid form. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2- enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered with or without a gastric acid reducing agent (e.g., an H2 blocker, an antacid, or a PPI). Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered with or without an H2 blocker (e.g., famotidine, nizatidine, cimetidine, or ranitidine). In another embodiment of the method of treatment or the solid form for use, the solid form is administered with an H2 blocker. In another embodiment of the method of treatment or the solid form for use, an H2 blocker is administered within 2 hours before or after administration of the solid form. In another embodiment of the method of treatment or the solid form for use, an H2 blocker is administered within 1 hour before or after administration of the solid form. In another embodiment of the method of treatment or the solid form for use, an H2 blocker is administered within 0.5 hour before or after administration of the solid form. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered with or without an antacid (e.g., aluminum hydroxide/magnesium hydroxide/simethicone or calcium carbonate). In another embodiment of the method of treatment or the solid form for use, the solid form is administered with an antacid. In another embodiment of the method of treatment or the solid form for use, an antacid is administered within 2 hours before or after administration of the solid form. In another embodiment of the method of treatment or the solid form for use, an antacid is administered within 1 hour before or after administration of the solid form. In another embodiment of the method of treatment or the solid form for use, an antacid is administered within 0.5 hour before or after administration of the solid form. Preferably, the solid form is 7-[[(1S)-1-[4-[(1S)-2-cyclopropyl-1-(4-prop enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered with or without a PPI (e.g., dexlansoprazole, esomeprazole, lansoprazole, omeprazole, pantoprazole sodium, or rabeprazole). In another embodiment of the method of treatment or the solid form for use, a PPI is administered within 2 hours before or after administration of the solid form. In another embodiment of the method of treatment or the solid form for use, a PPI is administered within 1 hour before or after administration of the solid form. In another embodiment of the method of treatment or the solid form for use, a PPI is administered within 0.5 hour before or after administration of the solid form. Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered simultaneous, separate or sequential with a gastric acid reducing agent (e.g., an H2 blocker, an antacid, or a PPI). Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered simultaneous, separate or sequential with an H2 blocker (e.g., famotidine, nizatidine, cimetidine, or ranitidine). Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered simultaneous, separate or sequential with an antacid (e.g., aluminum hydroxide/magnesium hydroxide/simethicone or calcium carbonate). Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

In another embodiment of the method of treatment or the solid form for use, the solid form is administered simultaneous, separate or sequential with a PPI (e.g., dexlansoprazole, esomeprazole, lansoprazole, omeprazole, pantoprazole sodium, or rabeprazole). Preferably, the solid form is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). More preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2). Even more preferably, the solid form is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Various aspects of the invention are set forth in the following numbered clauses.

Clause 1. A solid form of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and a dihydroxybenzoic acid selected from 2,5-dihydroxybenzoic acid, 2,4-dihydroxybenzoic acid, and 2,3-dihydroxybenzoic acid.

Clause 2. The solid form of clause 1, wherein the solid form is a crystalline solid form.

Clause 3. The solid form of clause 1 or clause 2, wherein the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the dihydroxybenzoic acid are in a molar ratio of about 1:2.

Clause 4. The solid form of any one of clauses 1-3, wherein the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and the dihydroxybenzoic acid are in a molar ratio of 1:2.

Clause 5. The solid form of any one of clauses 1-4, that is a crystalline solid form of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,5-dihydroxybenzoic acid.

Clause 6. The solid form of any one of clauses 1-5, characterized by an X-ray powder diffraction pattern using CuKa radiation having at least one peak at diffraction angle 2-theta of 7.2°, 9.0°, 9.5°, 10.9°, 11.7°, 14.5°, 15.7°, 16.8°, 17.2°, 19.2°, 20.8°, 24.1°, 24.7°, or 25.8° (±0.2°, respectively).

Clause 7. The solid form of any one of clauses 1-6, characterized by an X-ray powder diffraction pattern using CuKa radiation having a peak at diffraction angle 2-theta of 9.0° in combination with at least one peak selected from 7.2°, 9.5°, 10.9°, 11.7°, 14.5°, 15.7°, 16.8°, 17.2°, 19.2°, 20.8°, 24.1°, 24.7°, or 25.8° (±0.2°, respectively).

Clause 8. The solid form of any one of clauses 1-7, characterized by an X-ray powder diffraction pattern using CuKa radiation having a peak at diffraction angle 2-theta of 9.0°±0.2° in combination with at least one peak selected from 7.2°±0.2°, 9.5°±0.2°, and 11.7°±0.2°.

Clause 9. The solid form of any one of clauses 1-8, characterized by an X-ray powder diffraction pattern using CuKa radiation having at least peaks at diffraction angle 2-theta of 7.2°, 9.0°, 9.5°, 10.9°, 11.7°, 14.5°, 15.7°, 16.8°, 17.2°, 19.2°, 20.8°, 24.1°, 24.7°, and 25.8° (±0.2°, respectively).

Clause 10. The solid form of any one of clauses 1-9, characterized by a $^{13}C$ solid state NMR (100.6 MHz) spectrum which comprises at least one peak referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, or 175.2 ppm (±0.2 ppm, respectively).

Clause 11. The solid form of any one of clauses 1-10, characterized by a $^{13}C$ solid state NMR (100.6 MHz) spectrum which comprises at least one peak referenced to the high-field resonance of adamantane (d=29.5 ppm) at: 12.8, 23.9, 41.9, 68.1, 149.4, or 155.1 ppm (±0.2 ppm, respectively).

Clause 12. The solid form of any one of clauses 1-11, characterized by a $^{13}C$ solid state NMR (100.6 MHz) spectrum which comprises peaks referenced to the high-field resonance of adamantane (d=29.5 ppm) at: 12.8, 23.9, 41.9, 68.1, 149.4, and 155.1 ppm (±0.2 ppm, respectively).

Clause 13. The solid form of any one of clauses 1-12, characterized by a $^{13}C$ solid state NMR (100.6 MHz) spectrum which comprises peaks referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, and 175.2 ppm (±0.2 ppm, respectively).

Clause 14. The solid form of any one of clauses 1-4, that is a crystalline solid form of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one and 2,4-dihydroxybenzoic acid.

Clause 15. The solid form of any one of clauses 1-4, that is a crystalline solid form of 7-[[(1S)-1-[4-[(1S)-2-cyclopropyl-1-(4-prop-2-enoylpiperazin yl)ethyl]phenyl]ethyl]amino]-1-ethyl-4H-pyrimido[4,5-d][1,3]oxazin-2-one and 2,3-dihydroxybenzoic acid.

Clause 16. The solid form of any one of clauses 1-4 or clause 15, characterized by an X-ray powder diffraction pattern using CuKa radiation having at least one peak at diffraction angle 2-theta of 7.5°±0.2°, 8.9°±0.2°, 9.3°±0.2°, 10.9°±0.2°, 11.5°±0.2°, 12.3°±0.2°, 14.0°±0.2°, 15.0°±0.2°, 16.6°±0.2°, 17.3°±0.2°, 18.7°±0.2°, 21.1°±0.2°, 23.7°±0.2°, 24.6°±0.2°, or 25.8°±0.2°.

Clause 17. The solid form of any one of clauses 1-4, clause 15, or clause 16, characterized by an X-ray powder diffraction (XRPD) pattern using CuKa radiation having a peak at diffraction angle 2-theta of 11.5°±0.2° in combination with at least one peak selected from 7.5°±0.2°, 8.9°±0.2°, 9.3°±0.2°, 10.9°±0.2°, 12.3°±0.2°, 14.0°±0.2°, 15.0°±0.2°, 16.6°±0.2°, 17.3°±0.2°, 18.7°±0.2°, 21.1°±0.2°, 23.7°±0.2°, 24.6°±0.2°, and 25.8°±0.2°.

Clause 18. The solid form of any one of clauses 1-4, or clauses 15-17, characterized by an X-ray powder diffraction (XRPD) pattern using CuKa radiation having a peak at diffraction angle 2-theta of 11.5°±0.2° in combination with at least one peak selected from 8.9°±0.2°, 15.0°±0.2°, and 24.6°±0.2°.

Clause 19. The solid form of any one of clauses 1-4 or clauses 15-18, characterized by an X-ray powder diffraction pattern using CuKa radiation having at least peaks at diffraction angle 2-theta of 7.5°±0.2°, 8.9°±0.2°, 9.3°±0.2°, 10.9°±0.2°, 11.5°±0.2°, 12.3°±0.2°, 14.0°±0.2°, 15.0°±0.2°, 16.6°±0.2°, 17.3°±0.2°, 18.7°±0.2°, 21.1°±0.2°, 23.7°±0.2°, 24.6°±0.2°, and 25.8°±0.2°.

Clause 20. A solid form that is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

Clause 21. A solid form that is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2).

Clause 22. A solid form that is 7-[[(1S)-1-[4-[(1S)-2-cyclopropyl-1-(4-prop enoylpiperazin-1-yl)ethyl]phenyl]ethyl]amino]-1-ethyl-4H-pyrimido[4,5-d][1,3]oxazin-2-one, 2,3-dihydroxybenzoic acid (1:2).

Clause 23. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

Clause 24. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2).

Clause 25. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2).

Clause 26. A pharmaceutical composition comprising a solid form of any one of clauses 1-25 or clauses 86-113, and a pharmaceutically acceptable carrier, diluent, or excipient.

Clause 27. The pharmaceutical composition of clause 26 formulated for oral administration.

Clause 28. The pharmaceutical composition of clause 26 or clause 27, wherein the pharmaceutically acceptable carrier, diluent, or excipient includes microcrystalline cellulose, mannitol, polyvinylpyrrolidone vinyl acetate, croscarmellose sodium, colloidal silica dioxide, or sodium stearyl fumarate.

Clause 29. A combination of a solid form of any one of clauses 1-25 or clauses 86-113, and one or more therapeutic agents selected from an antimetabolite agent, a hypomethylating agent, a Bcl-2 inhibitor, a mutant Flt3 inhibitor, and a deoxyadenosine analog and a platinum agent.

Clause 30. The combination of clause 29, wherein the one or more therapeutic agents is a deoxyadenosine analog and a platinum agent.

Clause 31. The combination of clause 30, wherein the deoxyadenosine analog is gemcitabine.

Clause 32. The combination of clause 30, wherein the platinum agent is cisplatin.

Clause 33. The combination of clause 30, wherein the deoxyadenosine analog is gemcitabine and the platinum agent is cisplatin.

Clause 34. A method of treating a cancer in a patient expressing an IDH mutation, comprising administering to a patient in need thereof a therapeutically effective amount of a solid form of any one of clauses 1-25 or clauses 86-113, a pharmaceutical composition of any one of clauses 26-28, or a combination of any one of clauses 29-33.

Clause 35. The method of clause 34, wherein the IDH mutation is an IDH1 mutation.

Clause 36. The method of clause 35, wherein the IDH1 mutation is an IDH1 R132 mutation.

Clause 37. The method of clause 34, wherein the IDH mutation is an IDH2 mutation.

Clause 38. The method of clause 37, wherein the IDH2 mutation is an IDH2 R140 mutation.

Clause 39. The method of clause 37, wherein the IDH2 mutation is an IDH2 R172 mutation.

Clause 40. The method of any one of clauses 34-39, wherein the cancer is a solid tumor cancer.

Clause 41. The method of clause 40, wherein the solid tumor cancer is cholangiocarcinoma, head and neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma.

Clause 42. The method of clause 41, wherein the solid tumor cancer is cholangiocarcinoma.

Clause 43. The method of any one of clauses 34-39, wherein the cancer is a hematologic malignancy.

Clause 44. The method of clause 43, wherein the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia.

Clause 45. The method of clause 44, wherein the hematologic malignancy is acute myeloid leukemia.

Clause 46. The method of any one of clauses 34-45, wherein the solid form of any one of clauses 1-25 or clauses 86-113, the pharmaceutical composition of any one of clauses 26-28, or the combination of any one of clauses 29-33 is administered with or without food.

Clause 47. The method of any one of clauses 34-46, wherein food may be consumed before (e.g., within 2 hours before) or after (e.g., within 1 hour after) the administration of the solid form of any one of clauses 1-25 or clauses 86-113, the pharmaceutical composition of any one of clauses 26-28, or the combination of any one of clauses 29-33.

Clause 48. The method of any one of clauses 34-47, wherein the solid form of any one of clauses 1-25 or clauses 86-113, the pharmaceutical composition of any one of clauses 26-28, or the combination of any one of clauses 29-33 is administered with or without a gastric acid reducing agent (e.g., an H2 blocker, an antacid, or a PPI).

Clause 49. The method of any one of clauses 34-47, wherein the solid form of any one of clauses 1-25 or clauses 86-113, the pharmaceutical composition of any one of clauses 26-28, or the combination of any one of clauses 29-33 is administered with or without an H2 blocker (e.g., famotidine, nizatidine, cimetidine, or ranitidine).

Clause 50. The method of any one of clauses 34-47, wherein the solid form of any one of clauses 1-25 or clauses 86-113, the pharmaceutical composition of any one of clauses 26-28, or the combination of any one of clauses 29-33 is administered with or without an antacid (e.g., aluminum hydroxide/magnesium hydroxide/simethicone or calcium carbonate).

Clause 51. The method of any one of clauses 34-47, wherein the solid form of any one of clauses 1-25 or clauses 86-113, the pharmaceutical composition of any one of clauses 26-28, or the combination of any one of clauses 29-33 is administered with or without a PPI (e.g., dexlansoprazole, esomeprazole, lansoprazole, omeprazole, pantoprazole sodium, or rabeprazole).

Clause 52. The method of any one of clauses 34-47, wherein the solid form of any one of clauses 1-25 or clauses 86-113, the pharmaceutical composition of any one of clauses 26-28, or the combination of any one of clauses 29-33 is administered simultaneous, separate or sequential with a gastric acid reducing agent (e.g., an H2 blocker, an antacid, or a PPI).

Clause 53. A solid form of any one of clauses 1-25 or clauses 86-113, a pharmaceutical composition of any one of clauses 26-28, or a combination of any one of clauses 29-33, for use in therapy.

Clause 54. A solid form of any one of clauses 1-25 or clauses 86-113, a pharmaceutical composition of any one of clauses 26-28, or a combination of any one of clauses 29-33, for use in treating a cancer in a patient expressing an IDH mutation.

Clause 55. The solid form for use according to clause 54, wherein the IDH mutation is an IDH1 mutation.

Clause 56. The solid form for use according to clause 55, wherein the IDH1 mutation is an IDH1 R132 mutation.

Clause 57. The solid form for use according to clause 54, wherein the IDH mutation is an IDH2 mutation.

Clause 58. The solid form for use according to clause 57, wherein the IDH2 mutation is an IDH2 R140 mutation.

Clause 59. The solid form for use according to clause 57, wherein the IDH2 mutation is an IDH2 R172 mutation.

Clause 60. The solid form for use according to any one of clauses 54-59, wherein the cancer is a solid tumor cancer.

Clause 61. The solid form for use according to clause 60, wherein the solid tumor cancer is cholangiocarcinoma, head and neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma.

Clause 62. The solid form for use according to clause 61, wherein the solid tumor cancer is cholangiocarcinoma.

Clause 63. The solid form for use according to any one of clauses 54-59, wherein the cancer is a hematologic malignancy.

Clause 64. The solid form for use according to clause 63, wherein the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia.

Clause 65. The solid form for use according to clause 64, wherein the hematologic malignancy is acute myeloid leukemia.

Clause 66. Use of a solid form of any one of clauses 1-25 or clauses 86-113, a pharmaceutical composition of any one of clauses 26-28, or combination of any one of clauses 29-33, in the manufacture of a medicament for treating a cancer in a patient expressing an IDH mutation.

Clause 67. The use of a solid form of clause 66, wherein the IDH mutation is an IDH1 mutation.

Clause 68. The use of a solid form of clause 67, wherein the IDH1 mutation is an IDH1 R132 mutation.

Clause 69. The use of a solid form of clause 66, wherein the IDH mutation is an IDH2 mutation.

Clause 70. The use of a solid form of clause 69, wherein the IDH2 mutation is an IDH2 R140 mutation.

Clause 71. The use of a solid form of clause 69, wherein the IDH2 mutation is an IDH2 R172 mutation.

Clause 72. The use of a solid form of any one of clauses 66-71, wherein the cancer is a solid tumor cancer.

Clause 73. The use of a solid form of clause 72, wherein the solid tumor cancer is cholangiocarcinoma, head and neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma.

Clause 74. The use of a solid form of clause 73, wherein the solid tumor cancer is cholangiocarcinoma.

Clause 75. The use of a solid form of any one of clauses 66-71, wherein the cancer is a hematologic malignancy.

Clause 76. The use of a solid form of clause 75, wherein the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia.

Clause 77. The use of a solid form of clause 76, wherein the hematologic malignancy is acute myeloid leukemia.

Clause 78. A process of preparing a solid form of any one of clauses 1-25, comprising: providing a solution comprising 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, a dihydroxybenzoic acid selected from 2,5-dihydroxybenzoic acid, 2,4-dihydroxy benzoic acid, and 2,3-dihydroxybenzoic acid, and a solvent; and precipitating from the solution the solid form.

Clause 79. The process of clause 78, wherein the solvent is acetonitrile.

Clause 80. The process of clause 78 or clause 79, wherein the solution is heated to above room temperature prior to the precipitation, preferably about 70° C.

Clause 81. The process of any one of clauses 78-80, wherein at least two equivalents of the dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

Clause 82. A solid form of any one of clauses 1-25, produced by a process comprising providing a solution of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, a dihydroxybenzoic acid selected from 2,5-dihydroxybenzoic acid, 2,4-dihydroxy benzoic acid, and 2,3-dihydroxybenzoic acid, and a solvent; and precipitating from the solution the solid form.

Clause 83. The solid form of clause 82, wherein the solvent is acetonitrile.

Clause 84. The solid form of clause 82 or clause 83, wherein the solution is heated to above room temperature prior to the precipitation, preferably about 70° C.

Clause 85. The solid form of any one of clauses 82-84, wherein at least two equivalents of the dihydroxybenzoic acid are used relative to the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

Clause 86. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Clause 87. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), characterized by at least one of:

(i) an X-ray powder diffraction pattern using CuKa radiation having at least one peak at diffraction angle 2-theta of 7.2°±0.2°, 9.0°±0.2°, 9.5°±0.2°, 10.9°±0.2°, 11.7°±0.2°, 14.5°±0.2°, 15.7°±0.2°, 16.8°±0.2°, 17.2°±0.2°, 19.2°±0.2°, 20.8°±0.2°, 24.1°±0.2°, 24.7°±0.2°, or 25.8°±0.2°; or (ii) a $^{13}$C solid state NMR (100.6 MHz) spectrum which comprises at least one peak referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, or 175.2 ppm (±0.2 ppm, respectively).

Clause 88. The solid form of clause 86 or clause 87, characterized by an X-ray powder diffraction pattern using CuKa radiation having at least one peak at diffraction angle 2-theta of 7.2°, 9.0°, 9.5°, 10.9°, 11.7°, 14.5°, 15.7°, 16.8°, 17.2°, 19.2°, 20.8°, 24.1°, 24.7°, or 25.8° (±0.2°, respectively).

Clause 89. The solid form of any one of clauses 86-88, characterized by an X-ray powder diffraction pattern using CuKa radiation having a peak at diffraction angle 2-theta of 9.0° in combination with at least one peak selected from 7.2°, 9.5°, 10.9°, 11.7°, 14.5°, 15.7°, 16.8°, 17.2°, 19.2°, 20.8°, 24.1°, 24.7°, or 25.8° (±0.2°, respectively).

Clause 90. The solid form of any one of clauses 86-89, characterized by an X-ray powder diffraction pattern using CuKa radiation having a peak at diffraction angle 2-theta of 9.0°±0.2° in combination with at least one peak selected from 7.2°±0.2°, 9.5°±0.2°, and 11.7°±0.2°.

Clause 91. The solid form of any one of clauses 86-90, characterized by an X-ray powder diffraction pattern using CuKa radiation having at least peaks at diffraction angle 2-theta of 7.2°, 9.0°, 9.5°, 10.9°, 11.7°, 14.5°, 15.7°, 16.8°, 17.2°, 19.2°, 20.8°, 24.1°, 24.7°, and 25.8° (±0.2°, respectively).

Clause 92. The solid form of clause 86, having an X-ray powder diffraction pattern substantially as shown in FIG. 1.

Clause 93. The solid form of any one of clauses 86-92, characterized by a $^{13}$C solid state NMR (100.6 MHz) spectrum which comprises at least one peak referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, or 175.2 ppm (±0.2 ppm, respectively).

Clause 94. The solid form of any one of clauses 86-93, characterized by a $^{13}$C solid state NMR (100.6 MHz) spectrum which comprises at least one peak referenced to the high-field resonance of adamantane (d=29.5 ppm) at: 12.8, 23.9, 41.9, 68.1, 149.4, or 155.1 ppm (±0.2 ppm, respectively).

Clause 95. The solid form of any one of clauses 86-94, characterized by a $^{13}$C solid state NMR (100.6 MHz) spectrum which comprises peaks referenced to the high-field resonance of adamantane (d=29.5 ppm) at: 12.8, 23.9, 41.9, 68.1, 149.4, and 155.1 ppm (±0.2 ppm, respectively).

Clause 96. The solid form of any one of clauses 86-95, characterized by a $^{13}$C solid state NMR (100.6 MHz) spectrum which comprises peaks referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, and 175.2 ppm (±0.2 ppm, respectively).

Figure 2:
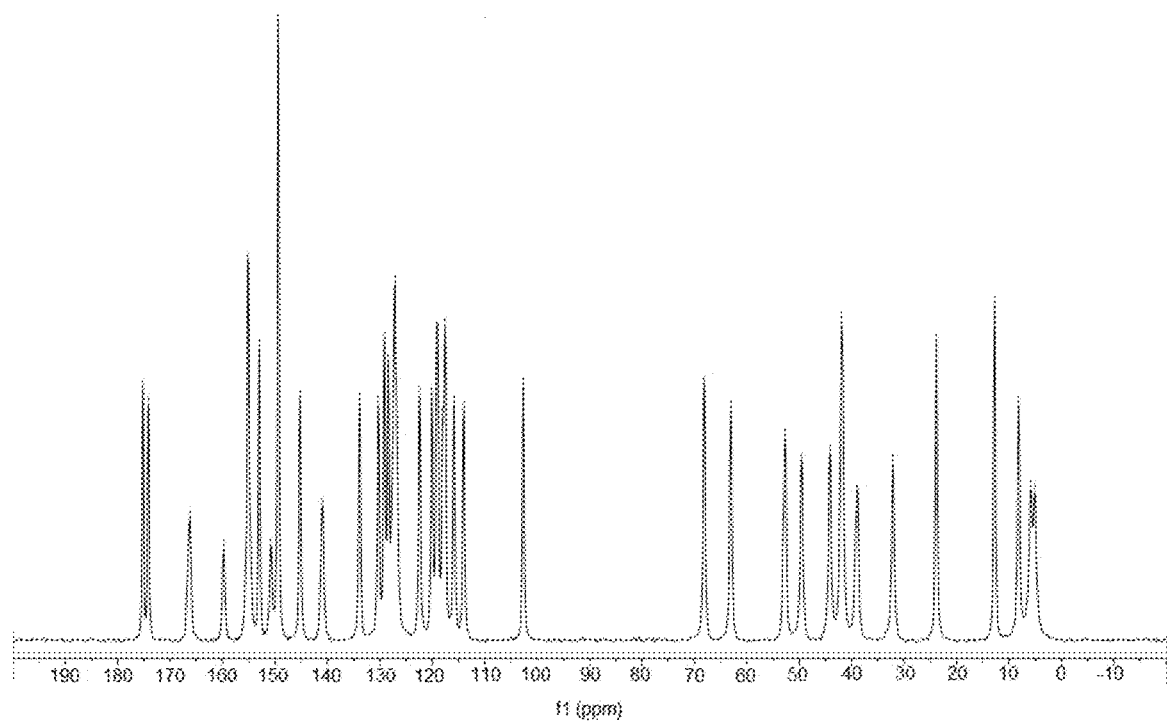
FIG. 2 is a solid state NMR spectrum of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I.

Clause 97. The solid form of any one of clauses 86-92, having a $^{13}$C solid state NMR spectrum substantially as shown in FIG. 2.

Clause 98. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II.

Clause 99. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II acetone solvate.

Clause 100. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II MEK solvate.

Clause 101. The solid form of any one of clauses 98-100, characterized by an X-ray powder diffraction pattern using CuKa radiation having at least one peak at diffraction angle 2-theta of 4.9°, 6.5°, 7.5°, 8.2°, 9.9°, 12.0°, 12.7°, 14.8°, 15.0°, 15.4°, 16.0°, 17.0°, 17.4°, or 19.6° (±0.2°, respectively).

Clause 102. The solid form of any one of clauses 98-101, characterized by an X-ray powder diffraction pattern using CuKa radiation having a peak at diffraction angle 2-theta of 6.5° in combination with at least one peak selected from 4.9°, 7.5°, 8.2°, 9.9°, 12.0°, 12.7°, 14.8°, 15.0°, 15.4°, 16.0°, 17.0°, 17.4°, and 19.6° (±0.2°, respectively).

Clause 103. The solid form of any one of clauses 98-102, characterized by an X-ray powder diffraction pattern using CuKa radiation having a peak at diffraction angle 2-theta of 6.5° in combination with at least one peak selected from 4.9°, 8.2°, and 12.7° (±0.2°, respectively).

Clause 104. The solid form of any one of clauses 98-103, characterized by an X-ray powder diffraction pattern using CuKa radiation having at least peaks at diffraction angle 2-theta of 4.9°, 6.5°, 7.5°, 8.2°, 9.9°, 12.0°, 12.7°, 14.8°, 15.0°, 15.4°, 16.0°, 17.0°, 17.4°, and 19.6° (±0.2°, respectively).

Figure 3:
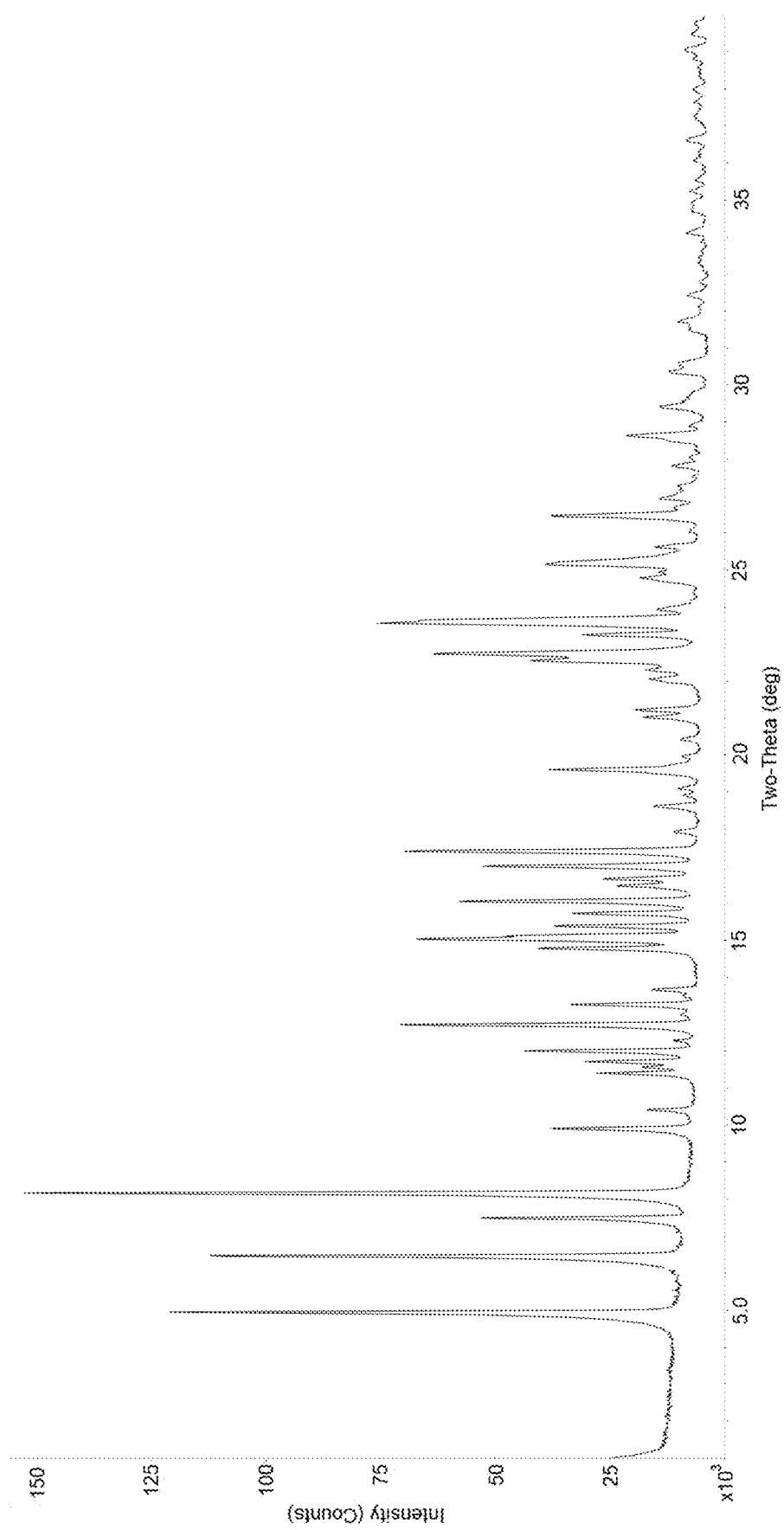
FIG. 3 is an XRPD pattern of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II acetone solvate.

Clause 105. The solid form of clause 98, having an X-ray powder diffraction pattern substantially as shown in FIG. 3.

Clause 106. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III.

Clause 107. The solid form of clause 106, characterized by an X-ray powder diffraction pattern using CuKa radiation having at least one peak at diffraction angle 2-theta of 5.5°, 8.5°, 11.0°, 11.9°, 12.4°, 14.0°, 14.3°, 16.3°, 16.6°, 17.0°, or 19.1° (±0.2°, respectively).

Clause 108. The solid form of clause 106 or clause 107, characterized by an X-ray powder diffraction pattern using CuKa radiation having a peak at diffraction angle 2-theta of 5.5°±0.2° in combination with at least one peak selected from 8.5°, 11.0°, 11.9°, 12.4°, 14.0°, 14.3°, 16.3°, 16.6°, 17.0°, and 19.1° (±0.2°, respectively).

Clause 109. The solid form of any one of clauses 106-108, characterized by an X-ray powder diffraction pattern using CuKa radiation having a peak at diffraction angle 2-theta of 5.5° in combination with at least one peak selected from 8.5°, 11.0°, and 11.9° (±0.2°, respectively).

Clause 110. The solid form of any one of clauses 106-109, characterized by an X-ray powder diffraction pattern using CuKa radiation having at least peaks at diffraction angle 2-theta of 5.5°, 8.5°, 11.0°, 11.9°, 12.4°, 14.0°, 14.3°, 16.3°, 16.6°, 17.0°, and 19.1° (±0.2°, respectively).

Figure 4:
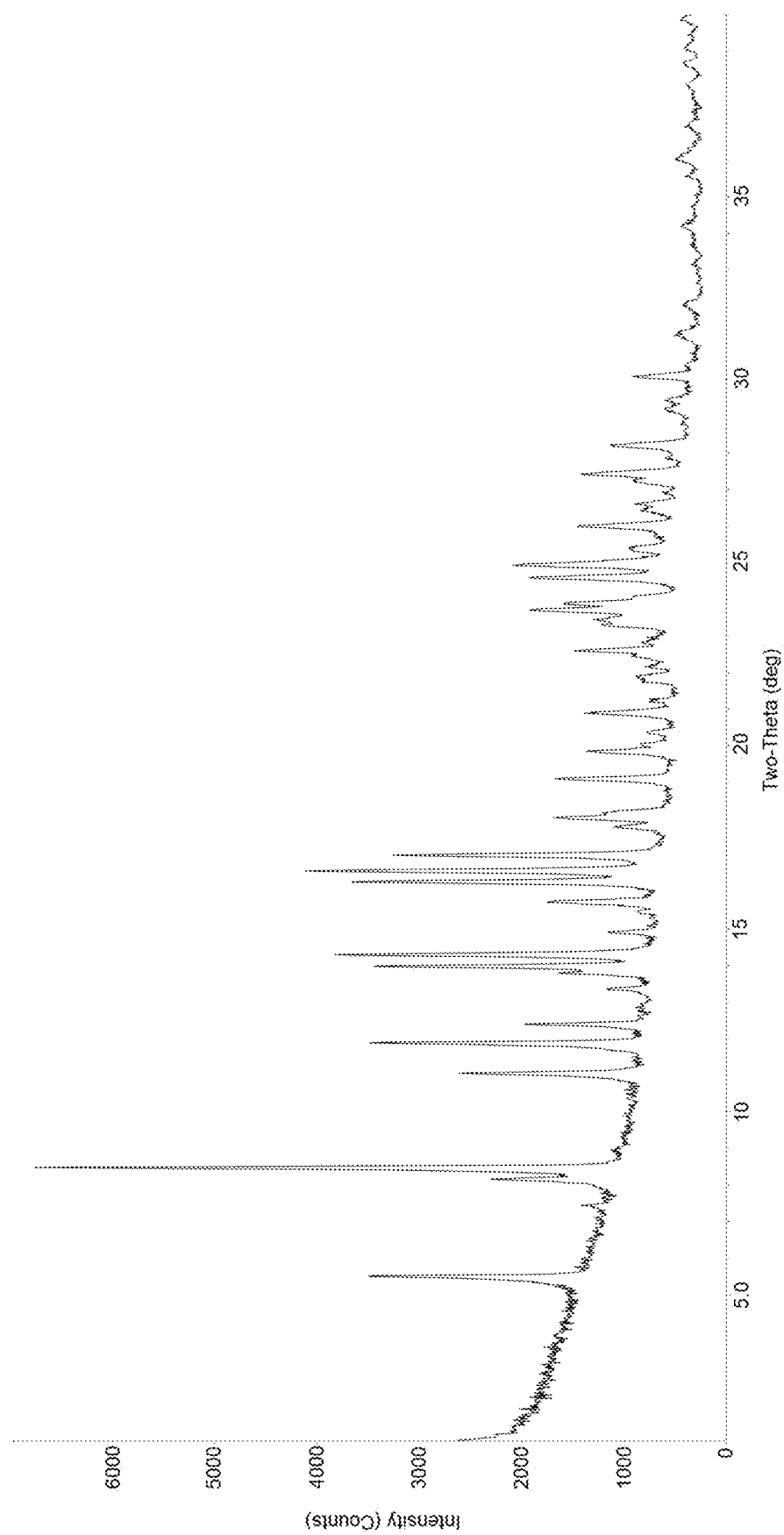
FIG. 4 is an XRPD pattern of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III.

Clause 111. The solid form of clause 106, having an X-ray powder diffraction pattern substantially as shown in FIG. 4.

Clause 112. A solid form that is amorphous 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

Figure 5:
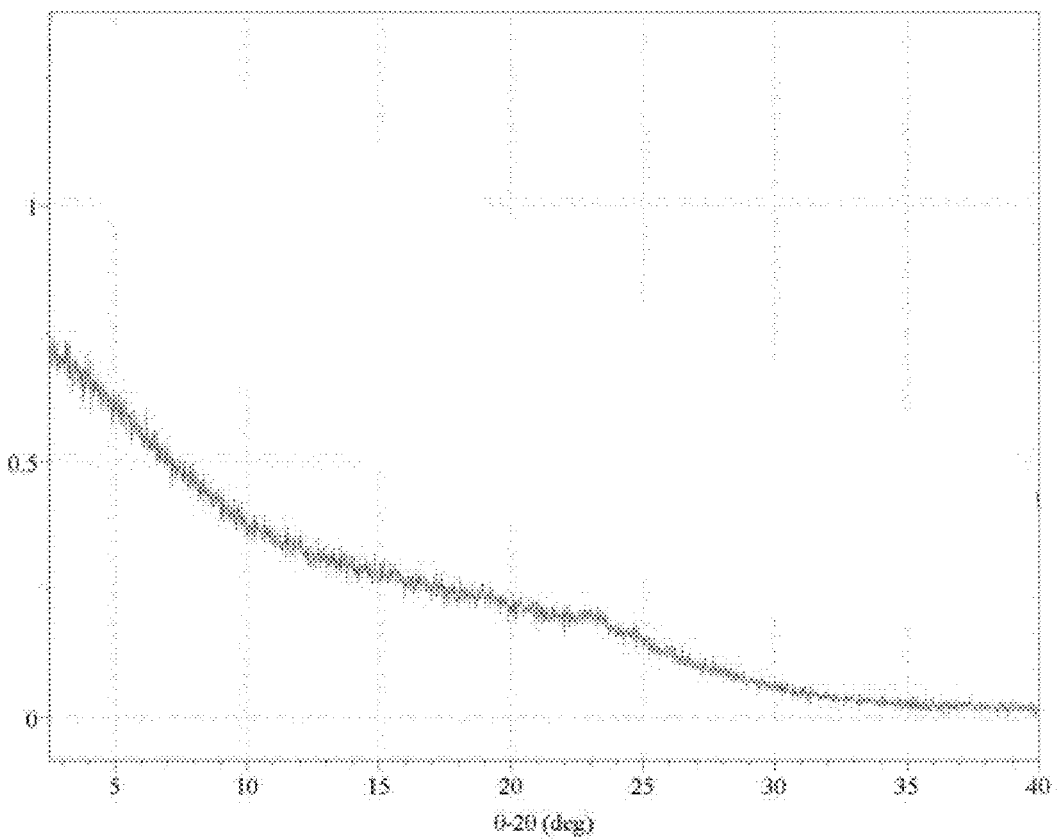
FIG. 5 is an XRPD pattern of amorphous 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

Clause 113. The solid form of clause 112, having an X-ray powder diffraction pattern substantially as shown in FIG. 5.

The term "about" means±10% of the numerical value recited.

The terms "acute myeloid leukemia," "acute myelogenous leukemia," and "acute nonlymphocytic leukemia" are synonymous.

The term "advanced cancer" refers to cancer that has spread to lymph nodes or to other tissues outside of the cancer's point of origin. For example, advanced AML is AML that has spread to a tissue outside of the blood or the bone marrow.

The term "anhydrous crystalline solid" refers to a crystalline solid that does not have water associated in the crystal lattice. An anhydrous crystalline solid may still contain residual water, which is not part of the crystal structure but may be adsorbed on the surface or absorbed in disordered regions of the crystal.

The term "anhydrous non-solvated crystalline solid" refers to a crystalline solid that does not have water or organic solvent associated in the crystal lattice. An anhydrous non-solvated crystalline solid may still contain residual water or organic solvent, which is not part of the crystal structure but may be adsorbed on the surface or absorbed in disordered regions of the crystal.

The term "cancer" refers to or describe the physiological condition in patients that is typically characterized by unregulated cell proliferation. Included in this definition are benign and malignant cancers.

The term "crystalline solid isostructural solvate" refers to crystalline solid that can associate different organic solvents in the crystal lattice without significant distortion of the crystal lattice structure.

The term "crystalline solid solvate" refers to a crystalline solid having an organic solvent associated in the crystal lattice.

The term "frontline cancer" means that the human cancer patient has never been treated for the cancer being treated.

The term "gentisic acid" refers to 2,5-dihydroxybenzoic acid, which can be represented by the structure:

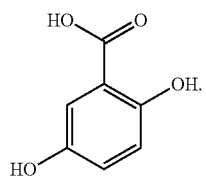

The term "hematologic malignancy" relates to cancer that originated in the blood, bone marrow, lymph node or lymphatic fluid.

The term "IDH1 R132 mutation" refers to an IDH1 mutation at amino acid residue 132 in a subject's IDH1 enzyme, as determined, e.g., in the subject's nucleic acid (e.g., DNA).

The term "IDH2 R140 mutation" refers to an IDH2 mutation at amino acid residue 140 in a subject's IDH2 enzyme, as determined, e.g., in the subject's nucleic acid (e.g., DNA).

The term "IDH2 R172 mutation" refers to an IDH2 mutation at amino acid residue 172 in a subject's IDH2 enzyme, as determined, e.g., in the subject's nucleic acid (e.g., DNA).

The term "identified as having an IDH1 R132 mutation" means that nucleic acid (e.g., DNA) from the subject's tissue or cells (e.g., circulating tumor cells) has been analyzed to determine if a subject has an IDH1 R132 mutation. For example, the subject's blood cells, bone marrow cells, blood cells, bone marrow, or solid tissue has been analyzed for an IDH1 R132 mutation.

The term "identified as having an IDH2 R140 mutation" means that nucleic acid (e.g., DNA) from the subject's tissue or cells has been analyzed to determine if a subject has an IDH2 R140 mutation. For example, the subject's blood cells, bone marrow cells, blood cells, bone marrow, or solid tissue has been analyzed for an IDH2 R140 mutation.

The term "identified as having an IDH2 R172 mutation" means that nucleic acid (e.g., DNA) from the subject's tissue or cells has been analyzed to determine if a subject has an IDH2 R172 mutation. For example, the subject's blood cells, bone marrow cells, blood cells, bone marrow, or solid tissue has been analyzed for an IDH2 R172 mutation.

The term "non-solvated crystalline solid" refers to a crystalline solid that does not have organic solvent associated in the crystalline lattice. A non-solvated crystalline solid may still contain residual organic solvent, which is not part of the crystal structure but may be adsorbed on the surface or absorbed in disordered regions of the crystal.

The term "patient" means mammal and "mammal" includes, but is not limited to, a human. A human is a preferred patient.

The term "pharmaceutically acceptable carrier, diluent, or excipient" refers to a medium generally accepted in the art for the delivery of biologically active agents to mammals, e.g., humans.

The term "pharmaceutically acceptable salts" or "a pharmaceutically acceptable salt" refers to the relatively non-toxic, inorganic and organic salt or salts of a therapeutic agent (S. M. Berge, et al., "Pharmaceutical Salts", *Journal of Pharmaceutical Sciences*, Vol 66, No. 1, January 1977).

The term "refractory cancer" refers to cancer that has been treated, but the human cancer patient did not respond to treatment.

The term "relapsed cancer" means that the human cancer patient responded to treatment for a period of time, but that the cancer has reoccurred.

The term "solid tumor cancer" means that the cancer originated in a tissue that is not blood, bone marrow, lymph node or lymphatic fluid.

The term "solid tumor tissue" refers to tissue that is not hematologic tissue. Non-limiting examples of solid tissue are cholangial tissue, pancreatic tissue, head tissue, neck tissue, hepatic tissue, skin tissue, astrocytomal tissue, oligodendroglial tissue, glial tissue, brain tissue, bladder tissue, colorectal tissue, lung tissue, and sinonasal undifferentiated cancer tissue.

The term "therapeutically effective amount" means the amount of a solid form as described herein administered to the subject that will elicit the biological or medical response of or desired therapeutic effect on a subject. A therapeutically effective amount can be readily determined by the attending clinician, as one skilled in the art, by the use of known techniques and by observing results obtained under analogous circumstances. In determining the effective amount for a subject, a number of factors are considered by the attending clinician, including, but not limited to: size, age, and general health of the individual subject; the specific disease or disorder involved; the degree of or involvement or the severity of the disease or disorder; the response of the individual subject; the particular compound administered; the mode of administration; the bioavailability characteristics of the preparation administered; the dose regimen selected; the use of concomitant medication; and other relevant circumstances.

The terms "treatment," "treat," "treating," and the like, are meant to include slowing, stopping, or reversing the progression of cancer. These terms also include alleviating, ameliorating, attenuating, eliminating, or reducing one or more symptoms of a disorder or condition, even if the cancer is not actually eliminated and even if progression of the cancer is not itself slowed, stopped, or reversed.

The following examples are provided to illustrate the invention and are not intended to be limiting in any way.

The XRPD patterns of crystalline solids of Example 2 and Example 7 are obtained on a Bruker D8 Endeavor X-ray powder diffractometer, equipped with a CuKα (1.5418 Å) source and a Linxeye detector, operating at 40 kV and 40 mA. The sample is scanned between 4 and 42 2θ°, with a step size of 0.009 2θ° and a scan rate of 0.5 seconds/step, and using 0.3° primary slit opening, and 3.9° particle size distribution (PSD) opening. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°.

The XRPD patterns of crystalline solids of Example 3 and Example 4 are obtained with a PANalytical X'Pert PRO MPD or Empyrean diffractometer using an incident beam of Cu radiation produced using an Optix long, fine-focus source. An elliptically graded multilayer mirror was used to focus CuKα (1.5418 Å) X-ray radiation through the specimen and onto the detector. Prior to the analysis, a silicon specimen (NIST SRM 640f) is analyzed to verify the observed position of the Si (111) peak is consistent with the NIST certified position. A specimen of the sample is sandwiched between 3-μm-thick films and analyzed in transmission geometry. A beam-stop, short antiscatter extension, and antiscatter knife edge are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 5.5. Crystal peak positions are determined in MDI-Jade v7.9.9.

For All XRPD examples in this document, it is well known in the crystallographic art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Solid state NMR (ssNMR) is obtained on Bruker Avance III HD with a Bruker Ultrashield 400WB Plus magnet operating at a frequency of 100.6 MHz. The probe employed is a Bruker MAS 4 BL CP BB DVT N-P/H. Acquisitional parameters are as follows: 7776 scans, 34 ms acquisition time, 4.2 s interpulse delay, 10 kHz magic angle spinning (MAS) frequency, 1.5 ms contact time, and a SPINAL64 decoupling scheme. The data are externally referenced to adamantane at 29.5 ppm.

TGA/DSC combination analyses are performed using a Mettler Toledo TGA/DSC3+ analyzer. Temperature and enthalpy adjustments are performed using phenyl salicylate, indium, tin, and zinc, and then verified with indium. Balance is verified with calcium oxalate. The sample is placed in an aluminum pan. The pan is hermetically sealed, the lid pierced, then inserted into the TG furnace. A weighed aluminum pan configured as the sample pan is placed on the reference platform. The furnace is heated under nitrogen.

EXAMPLE 1

Crystalline 7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one The title compound may be prepared as described in WO/18/111707.

EXAMPLE 2

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I

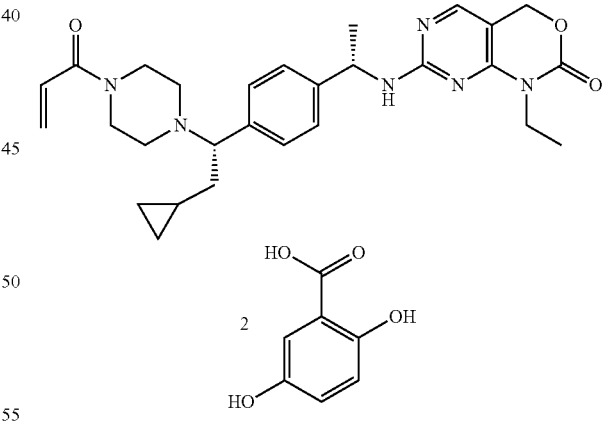

7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one (17.9 g, 35.5 mmol) is suspended in acetonitrile (250 mL) at 70° C. while stirring at 700 rpm. 2,5-Dihydroxybenzoic acid (12.05 g, 78.1 mmol) is added to the solution. The reaction mixture becomes a clear solution before a white solid precipitates. The heat source is removed, and the mixture is stirred at room temperature, becoming an off-white solid slurry. The solid is isolated by filtration under vacuum, rinsed with acetonitrile (50 mL), dried under vacuum and nitrogen for 15 min, and then dried in a vacuum oven at 60° C. overnight to give the title compound (27.3 g, 94.7% yield). $^{13}$C Solid state NMR (100.6 MHz) δ 175.2, 174.2, 166.3, 159.8, 155.1, 153.0, 150.8, 149.4, 145.2, 141.0, 133.9, 130.3, 129.2, 128.4, 127.6, 127.1, 126.7, 122.4, 120.1, 119.3, 119.0, 118.0, 117.6, 115.9, 114.0, 102.7, 68.1, 63.1, 52.7, 49.6, 44.1, 41.9, 39.0, 32.1, 23.9, 12.8, 8.2, 5.9, 5.1 ppm.

XRPD

A prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is characterized by an XRPD pattern using CuKα radiation as having diffraction peaks (2-theta values) as described in Table 1 below, and in particular having a peak at 9.0 in combination with one or more of the peaks selected from 7.2, 9.5, and 11.7; with a tolerance for the diffraction angles of 0.2 degrees.

TABLE 1

XRPD peaks, Form I

| Peak | Angle (°2-Theta) +/− 0.2° | Relative Intensity (% of most intense peak) |
|---|---|---|
| 1 | 7.2 | 35.0% |
| 2 | 9.0 | 75.5% |
| 3 | 9.5 | 46.9% |
| 4 | 10.9 | 37.1% |
| 5 | 11.7 | 88.1% |
| 6 | 14.5 | 39.7% |
| 7 | 15.7 | 37.5% |
| 8 | 16.8 | 58.4% |
| 9 | 17.2 | 57.1% |
| 10 | 19.2 | 60.6% |
| 11 | 20.8 | 26.7% |
| 12 | 24.1 | 70.9% |
| 13 | 24.7 | 100.0% |
| 14 | 25.8 | 49.2% |

Single Crystal Structure Analysis

A vial is charged with 12.0 mg of a prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I and dissolved in ethanol (1 ml). The vial opening is sealed with aluminum foil and pierced once. The sample is held at 10° C. and evaporated to near completion over the course of twelve days upon which suitable crystals are isolated. A colorless needle having approximate dimensions of 0.25×0.05×0.02 mm$^3$, is mounted on a polymer loop in random orientation. Preliminary examination and data collection are performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection are obtained from least-squares refinement using the setting angles of 10655 reflections in the range 4.2920° <θ<75.6600°. The space group is determined by the program CRYSALISPRO to be C2 (international tables no. 5). The data are collected to a maximum diffraction angle (2θ) of 151.682° at room temperature.

The structure of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is determined to be an anhydrous non-solvated crystalline solid, composed of one 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one di-cation and two gentisate anions in the asymmetric unit. The absolute configuration is determined from the crystal structure and the molecule is found to bond in the S configuration at both chiral centers.

TGA

A prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is analyzed by thermogravimetric analysis (TGA). Form I exhibits a weight loss of 0.6% from 45-100° C., likely due to loss of moisture; consistent with an anhydrous form.

EXAMPLE 3

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II acetone solvate Example 2 (52 mg, 0.064 mmol) is suspended in acetone (4 mL) and heated to 55° C. to form a clear solution. The solution is filtered with a 0.2 μm nylon syringe filter, the solution is quickly cooled to 0° C., and precipitation is observed. The material is stored at 10-25° C. for 7 days and the solids are isolated as wet by vacuum filtration.

XRPD

A prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II acetone solvate is characterized by an XRPD pattern using CuKα radiation as having diffraction peaks (2-theta values) as described in Table 2 below, and in particular having a peak at 6.5 in combination with one or more of the peaks selected from the group consisting of 4.9, 8.2, and 12.7; with a tolerance for the diffraction angles of 0.2 degrees.

TABLE 2

XRPD Peaks, Form II

| Peak | Angle (°2-Theta) +/− 0.2° | Relative Intensity (% of most intense peak) |
|---|---|---|
| 1 | 4.9 | 76.4% |
| 2 | 6.5 | 70.9% |
| 3 | 7.5 | 30.5% |
| 4 | 8.2 | 100.0% |
| 5 | 9.9 | 21.1% |
| 6 | 12.0 | 24.2% |
| 7 | 12.7 | 43.8% |
| 8 | 14.8 | 23.9% |
| 9 | 15.0 | 42.2% |
| 10 | 15.4 | 21.6% |
| 11 | 16.0 | 34.2% |
| 12 | 17.0 | 30.5% |
| 13 | 17.4 | 43.3% |
| 14 | 19.6 | 22.6% |

TGA

A prepared sample of crystalline 7-[[(1S)-1-[4-[(1S)-2-cyclopropyl-1-(4-prop enoylpiperazin-1-yl)ethyl]phenyl]

ethyl]amino]-1-ethyl-4H-pyrimido[4,5-d][1,3]oxazin-2-one, 2,5-dihydroxybenzoic acid (1:2) Form II acetone solvate is analyzed by thermogravimetric analysis (TGA). Form II acetone solvate exhibits a weight loss of about 7.1% from 37-140° C., corresponding to about 1.1 moles of acetone.

EXAMPLE 4

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II acetone solvate, is dried at 45° C. under vacuum for 1 day.

XRPD

A prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III is characterized by an XRPD pattern using CuKα radiation as having diffraction peaks (2-theta values) as described in Table 3 below, and in particular having a peak at 5.5 in combination with one or more of the peaks selected from the group consisting of 8.5, 11.0, and 11.9; with a tolerance for the diffraction angles of 0.2 degrees.

TABLE 3

| XRPD Peaks, Form III | | |
|---|---|---|
| Peak | Angle (°2-Theta) +/− 0.2° | Relative Intensity (% of most intense peak) |
| 1 | 5.5 | 35.60% |
| 2 | 8.5 | 100.00% |
| 3 | 11.0 | 29.90% |
| 4 | 11.9 | 45.40% |
| 5 | 12.4 | 19.90% |
| 6 | 14.0 | 46.20% |
| 7 | 14.3 | 52.60% |
| 8 | 16.3 | 50.50% |
| 9 | 16.6 | 58.00% |
| 10 | 17.0 | 42.10% |
| 11 | 19.1 | 19.20% |

TGA

A prepared sample of crystalline 7-[[(1S)-1-[4-[(1S)-2-cyclopropyl-1-(4-prop enoylpiperazin-1-yl)ethyl]phenyl]ethyl]amino]-1-ethyl-4H-pyrimido[4,5-d][1,3]oxazin one, 2,5-dihydroxybenzoic acid (1:2) Form III is analyzed by thermogravimetric analysis (TGA). Form III exhibits a weight loss of 0.6% from 47-150° C., consistent with an anhydrous form.

EXAMPLE 5

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II MEK solvate Example 2 is stirred in methyl ethyl ketone (MEK) at room temperature for 1 day. The resulting precipitated solids are collected by filtration through a 0.22 μm nylon centrifuge tube filter to give the title compound.

EXAMPLE 6

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form III Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form II MEK solvate, is dried under vacuum at 75° C. for 5 hours to give the title compound.

EXAMPLE 7

Amorphous 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2)

7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) (about 340 mg, 0.44 mmol) is dissolved in a minimum amount of EtOH to dissolve the material, evaporated to dryness at 55° C., and dried under vacuum at room temperature for 1 day to give the amorphous title compound.

EXAMPLE 8

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2)

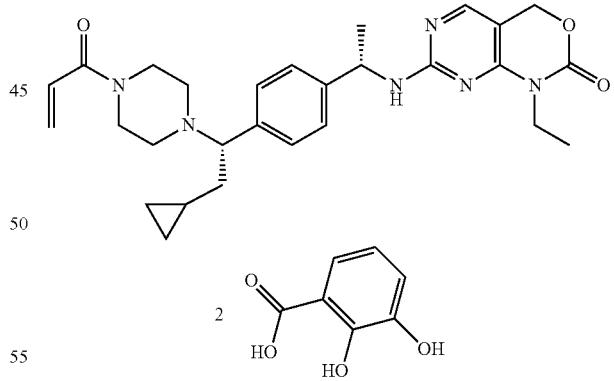

7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one (1.205 g, 2.45 mmol) is suspended in acetonitrile (20 mL) at 70° C. while stirring at 700 rpm. 2,3-Dihydroxybenzoic acid (0.832 g, 5.4 mmol) is added to the solution and the solids dissolve to give a clear light pink solution. The mixture is syringe filtered, the heat source is removed, and the mixture is stirred and allowed to cool to room temperature, becoming a solid slurry. The white solid is isolated by filtration under vacuum, rinsed with acetonitrile (5 mL), dried under vacuum and nitrogen for 15 min, and then dried in a vacuum oven at 60° C. overnight to give the title compound.

XRPD

A prepared sample of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2), is characterized by an XRPD pattern using CuKα radiation as having diffraction peaks (2-theta values) as described in Table 4 below, and in particular having a peak at 11.5 in combination with one or more of the peaks selected from 8.9, 15.0, and 24.6; with a tolerance for the diffraction angles of 0.2 degrees.

TABLE 4

XRPD peaks

| Peak | Angle (°2-Theta) +/− 0.2° | Relative Intensity (% of most intense peak) |
|---|---|---|
| 1 | 7.5 | 16.7% |
| 2 | 8.9 | 48.3% |
| 3 | 9.3 | 24.6% |
| 4 | 10.9 | 15.3% |
| 5 | 11.5 | 100.0% |
| 6 | 12.3 | 38.2% |
| 7 | 14.0 | 42.2% |
| 8 | 15.0 | 70.0% |
| 9 | 16.6 | 55.8% |
| 10 | 17.3 | 32.3% |
| 11 | 18.7 | 31.6% |
| 12 | 21.1 | 36.4% |
| 13 | 23.7 | 33.5% |
| 14 | 24.6 | 81.6% |
| 15 | 25.8 | 36.1% |

EXAMPLE 9

Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2)

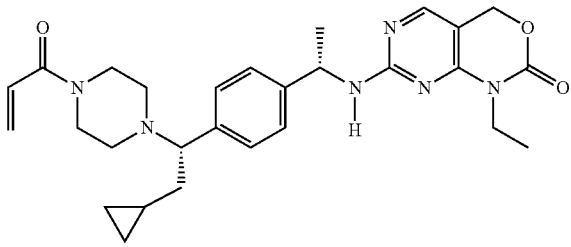

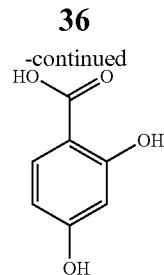

7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one (about 0.150 g, 2.45 mmol) is added to a saturated solution of 2,4-dihydroxybenzoic acid in acetonitrile (5 mL) at 60° C. The solid dissolves to a light brown solution and a white solid then precipitates. The white solid is isolated by filtration under vacuum, rinsed with acetonitrile (3 mL) and dried under vacuum and nitrogen for 15 min to give the title compound.

EXAMPLE 10

Non-Sink Dissolution Studies

Non-sink dissolution is performed by adding the test composition to a solution of 0.01 N HCl pH 2 (e.g., in a centrifuge tube) and analyzing for 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one solution concentration, by HPLC, at approximately time zero, 20 and 40 minutes. After approximately 40 minutes, a solution of fasted state simulated intestinal fluid (FaSSIF) pH 6.5, with 0.224 wt % bile salts, is added to the pH 2 solution. The 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one concentration is monitored, by HPLC, at approximately 50, 70, 90 and 120 minutes after time zero. At each timepoint the samples are centrifuged at 18,500 g-force for 3 minutes to remove undissolved solids from the sample. For analysis, a supernatant sample (100 μL) is diluted 5× using 1:1 acetonitrile/H$_2$O and analyzed. The non-sink dissolution test is completed at room temperature. See Table 5 below.

TABLE 5

Non-Sink Dissolution Results

| Test Composition | 7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one concentration via Microcentrifuge Assay at 30 minutes After FaSSIF Transfer (μg/mL) |
|---|---|
| TC1: Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one | 15.0 |

TABLE 5-continued

Non-Sink Dissolution Results

| Test Composition | 7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one concentration via Microcentrifuge Assay at 30 minutes After FaSSIF Transfer (µg/mL) |
|---|---|
| TC2: Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I | 19.2 |
| TC3: Crystalline 7-[[(1S)-1-[4-(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2) | 20.0 |
| TC4: Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2) | 27.5 |

"TC" refers to Test Composition

Table 5 shows increased solution concentration of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one at the 70 minute timepoint at elevated pH provided from TC2, TC3, and TC4 as compared to TC1.

EXAMPLE 11

Dog Pharmacokinetics Studies

Pharmacokinetic (PK) studies are conducted to evaluate pharmacokinetic performance of formulations containing crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I and formulations containing crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

Male beagle dogs are dosed with a single 5-mg/kg or 50 mg oral gavage administration of each formulation. Within each study, a cross-over design using 8 fasted dogs is utilized, with each period testing one formulation, and 4-7 days of washout period in between.

Studies are conducted at elevated gastric pH conditions or at conditions emulating human normal gastric pH environment. Two studies involve famotidine, mimicking patients taking acid-reducing agents; and one study uses pentagastrin to mimick human normal gastric pH environment or without PPIs intake.

Blood samples (about 1 mL, jugular vein) from each group are collected at 0, 0.25, 0.5, 1, 2, 4, 8, 12, and 24 hours post dose. Plasma is harvested from blood samples, diluted with water:phosphoric acid (75:25) at a plasma ratio of 100:1 and stored frozen until analyzed. For example, water:phosphoric acid (75:25, 10.0 µL) is added to whole blood (1000 µL) prior to harvesting plasma.

Plasma concentrations of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one are measured using a validated LC-MS/MS assay using the following conditions: Instrument autosampler is a Shimadzu SIL20AC; liquid chromatography pumps are Shimadzu LC20AD pumps; liquid chromatography controller is a Shimadzu CBM10A controller; and mass spectrometer is a Sciex API 5000. Liquid chromatography uses a mobile phase A of 1 M ammonium formate in water and mobile phase B of 1 M ammonium formate in 50% acetonitrile and 50% methanol with a Halo 5 C18, 20×2.1 mm column at a flow rate of 1.5 mL/minute at ambient temperature.

Pharmacokinetic parameters are reported in three significant figures, except for values relating to time, which are reported to two decimal points. The non-compartmental plasma pharmacokinetic parameters are calculated using Watson (version 7.5). Plasma concentrations of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one below the lower limit of quantitation (1 ng/mL or 1.98 nM) are assigned a value of zero.

Pharmacokinetic Study 1

Formulation 1. A suspension of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is prepared as follows. Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is weighed into a preparation container. The vehicle, 0.5% (w/v) methylcellulose A4M in purified water, is added slowly while pasting with a spatula to prepare a suspension (5 mg 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one/mL suspension). Pasting and stirring with a spatula is continued until the mixture is well dispersed. The mixture is then stirred with a magnetic stir bar and stir plate to ensure the formulation is homogenous.

Comparative Formulation 1. A suspension of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one is prepared as follows. Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one is weighed into a preparation container. The vehicle, 0.5% (w/v) methylcellulose A4M in purified water, is added slowly while pasting with a spatula to prepare a suspension (5 mg 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one active/mL suspension). Pasting and stirring with a spatula is continued until the mixture is well dispersed. The mixture is then stirred with a magnetic stir bar and stir plate to ensure the formulation is homogenous.

Study 1. Fasted dogs are dosed by oral gavage with a famotidine tablet (40 mg/animal). Water (5 to 10 mL) is optionally used to encourage swallowing of the famotidine tablet. Approximately 1 hour later, the dogs are dosed by oral gavage with Formulation 1 or Comparative Formulation 1. Prior to withdrawing the gavage tube after dosing with Formulation 1 or Comparative Formulation 1, the tube is flushed with water (approximately 15 mL). The dose level of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one active is 5 mg/kg. At selected timepoints, whole blood (approximately 1 mL) is drawn from the jugular vein and added to tubes (Covidien Monoject 2 mL, catalog #8881311149 and Greiner Bio-One 2 mL, catalog #454222) precoated with the anticoagulant tripotassium ethylenediaminetetraacetic acid ($K_3$EDTA). Within the study, a cross-over design using 8 fasted dogs is utilized, with each period testing one formulation and 7 days of washout period in between. The samples are collected at the following timepoints: 0, 0.25, 0.5, 1, 2, 4, 8, 12, and 24 hours post dose for each formulation tested.

TABLE 6

Summary of Mean ± SD Pharmacokinetic Parameters Following a Single 5 mg/kg Oral Dose in Male Beagle Dogs pretreated with Famotidine

| Parameter | Units | Dose (mg/kg) | Comparative Formulation 1 5 | | | Formulation 1 5 | | |
|---|---|---|---|---|---|---|---|---|
| | | | Mean | SD | n | Mean | SD | n |
| $AUC_{0-24}$ | ng * h/mL | | 282 | 112 | 8 | 1190 | 321 | 8 |
| $C_{max}$ | ng/mL | | 134 | 88.9 | 8 | 1440 | 714 | 8 |
| $T_{max}$ | Hours | | 0.313 | 0.116 | 8 | 0.281 | 0.0884 | 8 |

Abbreviations:
$AUC_{0-24}$ = area under the plasma concentration curve from time 0 to 24 hours post dose,
$C_{max}$ = maximum plasma concentration following oral dose,
n = number of animals,
SD = standard deviation,
$T_{max}$ = time of $C_{max}$.

Table 6 shows that dogs, when pre-treated with famotidine, had increased exposure to 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one via administration of Formulation 1. Formulation 1 had an exposure level, as measured by both $C_{max}$ and $AUC_{0-24}$, approximately 10- and 4-fold of that of Comparative Formulation 1.

Pharmacokinetic Study 2

Formulation 2. A tablet containing crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I is prepared as follows. Tablets are prepared by blending crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I with microcrystalline cellulose (MCC), mannitol, croscarmellose sodium, silica dioxide, and sodium stearyl fumarate. Following blending, the powder is compressed into slugs and milled to create free flowing granules. The granules are blended with croscarmellose sodium, silica dioxide and sodium stearyl fumarate to create the final blend. Tablets (containing 25 mg active) are made from the final blend by compressing ¹¹⁄₃₂" standard concave round tablets to approximately 8 kP hardness. See Table 7 below for the tablet formulation.

TABLE 7

Formulation 2 Tablet

| | Component | Grade | Percent Amount (wt %) | (mg) |
|---|---|---|---|---|
| Intragranular | Crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I | — | 20.2 | 40.3 |
| | Microcrystalline Cellulose | PH-101 | 45.8 | 91.7 |
| | Mannitol Spray Processed | Partek M-100 | 22.9 | 45.8 |
| | Croscarmellose Sodium (CCS) | Ac-di-sol | 6 | 12 |
| | Colloidal Sillica Dioxide | 200 m2/g (EMD milipore) | 0.8 | 1.5 |
| | Sodium Stearyl Fumarate (SSF) | Pruuv | 1 | 2 |
| Extragranular | Croscarmellose Sodium (CCS) | Ac-di-sol | 2.3 | 4.7 |
| | Colloidal Sillica Dioxide | 200 m2/g (EMD milipore) | 0.5 | 1 |
| | Sodium Stearyl Fumarate (SSF) | Pruuv | 0.5 | 1 |
| | Totals | | 100 | 200 |

Comparative Formulation 2. A capsule containing crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one is prepared as follows. Neat crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one powder is filled into Size #3 hypromellose opaque white capsule shells at 25 mg active strength per capsule.

Study 2. Dogs are dosed by oral gavage with a famotidine (40 mg) tablet. Approximately 1 hour later, the dogs are dosed by oral gavage with Formulation 2 or Comparative Formulation 2, followed by a flush of water (5-10 mL) to ensure swallowing. The dose level is 50 mg 7-[[(1S)-1-[4-[(1S)-2-cyclopropyl-1-(4-prop enoylpiperazin-1-yl)ethyl]phenyl]ethyl]amino]-1-ethyl-4H-pyrimido[4,5-d][1,3]oxazin one using 2 tablets. Whole blood (approximately 1 mL) is drawn from the jugular vein and added to tubes (Greiner Bio-One 2 mL, catalog #454428) precoated with the anticoagulant dipotassium ethylenediaminetetraacetic acid ($K_2$-EDTA). Within the study, a cross-over design using 8 fasted dogs is utilized with each period testing one formulation, and 4 days of washout period in between. The samples are collected at the following timepoints: 0, 0.25, 0.5, 1, 2, 4, 8, 12, and 24 hours post dose for each formulation tested.

TABLE 8

Summary of Mean ± SD Pharmacokinetic Parameters
Following a Single Oral Dose of 50 mg in Male
Beagle Dogs pretreated with Famotidine

| | Dose (mg) | Comparative Formulation 2 50 | | | Formulation 2 50 | | |
|---|---|---|---|---|---|---|---|
| Parameter | Units | Mean | SD | n | Mean | SD | n |
| $AUC_{0-24}$ | ng * h/mL | 288 | 78.4 | 8 | 1270 | 815 | 8 |
| $C_{max}$ | ng/mL | 53.5 | 26.1 | 8 | 929 | 606 | 8 |
| $T_{max}$ | Hours | 1.75 | 2.58 | 8 | 0.938 | 0.717 | 8 |

Table 8 shows that Formulation 2 has an exposure level approximately four-fold of that of Comparative Formulation 2, as measured by $AUC_{0-24}$.

Study 3: Pentagastrin (6 μg/kg) at a dose volume of 0.06 mL/kg is dosed by intramuscular injection in the dogs approximately 30 min prior to dosing with Formulation 2 or Comparative Formulation 2. Formulation 2 and Comparative Formulation 2 are added by oral gavage, followed by a flush of water (5-10 mL) to ensure swallowing. The dose level is 50 mg 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one. Whole blood (approximately 1 mL) is drawn from the jugular vein and added to tubes (Covidien Monoject 2 mL, catalog #8881311149) precoated with the anticoagulant $K_3EDTA$ and pre-spiked with 25% phosphoric acid (10 μL). Within the study, a cross-over design using 8 fasted dogs is utilized with each period testing one formulation, and 5 days of washout period in between. The samples are collected at the following timepoints: 0, 0.25, 0.5, 1, 2, 4, 8, 12, and 24 hours post dose.

TABLE 9

Summary of Mean ± SD Pharmacokinetic Parameters
Following a Single 50 mg Oral Dose in Male
Beagle Dogs pretreated with Pentagastrin

| | Dose Route Dose | Comparative Formulation 2 50 | | | Formulation 2 50 | | |
|---|---|---|---|---|---|---|---|
| Parameter | Units | Mean | SD | n | Mean | SD | n |
| $AUC_{0-24}$ | ng * hr/mL | 1300 | 719 | 7 | 1800 | 603 | 8 |
| $C_{max}$ | ng/mL | 977 | 636 | 7 | 1840 | 602 | 8 |
| $T_{max}$ | Hours | 0.393 | 0.134 | 7 | 0.406 | 0.129 | 8 |

* In Comparative group, dog D0005 not dosed with crystalline free base and therefore not included in the analysis.

As measured by $AUC_{0-24}$ in acidic conditions, Table 9 shows that Comparative Formulation 2 and Formulation 2 have more comparable exposure levels relative to exposures at elevated pH, suggesting the lower exposure of the 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one crystalline free base in the famotidine-pretreated dogs (Tables 6 and 8) is due to gastric pH-dependent solubility.

EXAMPLE 12

An Open-Label, Randomized, Crossover Study to Evaluate the Effect of Food and a Proton Pump Inhibitor on the Single-Dose Pharmacokinetics of crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2) Form I in Healthy Adult Subjects Study Rationale The aqueous solubility of Compound A is pH-dependent and therefore gastrointestinal (GI) pH modification may effect the solubility and subsequent oral absorption of Compound A from the GI tract. The primary objectives of the study are to evaluate and compare the single-dose PK of Compound A when administered as Compound A crystalline free base (in a capsule) versus Compound A digentisate Form I (in a tablet formulation) in healthy adult subjects under fasted conditions; to assess the effect of a standard low-fat meal on the single-dose PK of Compound A when administered as Compound A digentisate Form I (in a tablet formulation) in healthy adult subjects; and to assess the effect of a gastric pH change by a PPI (esomeprazole) on the single-dose PK of Compound A when administered as Compound A digentisate Form I (in a tablet formulation) under fasted conditions or fed conditions in healthy adult subjects.

Study Design

This is a Phase 1, open-label study in 4 groups of healthy adult subjects. Groups 1 and 2 have a randomized, 2-way crossover design and Groups 3 and 4 have a fixed-sequence design. Groups may be dosed in any order.

Group 1: Tablet Versus Capsule Comparison Group
(Fasted State)

In Group 1, single oral doses of Compound A are administered via capsules containing Compound A crystalline free base or tablets containing Compound A digentisate Form I on Days 1 and 4. Subjects are randomly assigned to 1 of 2 treatment sequences (AB or BA), according to a randomization scheme.

Treatment Sequence AB: On Day 1 (Period 1), a single oral dose of 300 mg Compound A (4×75-mg capsules) is administered in the morning following a fast of at least 10 hours prior to and 4 hours after dosing (Treatment A). On Day 4 (Period 2), a single oral dose of 300 mg Compound A (4×75-mg tablets) is administered in the morning following a fast of at least 10 hours prior to and 4 hours after dosing (Treatment B) at the same time of day (±1 hour) as the actual Day 1 Compound A dose.

Treatment Sequence BA: On Day 1 (Period 1), a single oral dose of 300 mg Compound A (4×75-mg tablets) is administered in the morning following a fast of at least 10 hours prior to and 4 hours after dosing (Treatment B). On Day 4 (Period 2), a single oral dose of 300 mg Compound A (4×75-mg capsules) is administered in the morning following a fast of at least 10 hours prior to and 4 hours after dosing (Treatment A) at the same time of day (±1 hour) as the actual Day 1 Compound A dose.

Group 2: Food-Effect Comparison Group (Tablet Formulation)

In Group 2, single oral doses of Compound A are administered via tablets containing Compound A digentisate Form I on Days 1 and 4 under fasted conditions and fed conditions. Subjects are randomly assigned to 1 of 2 treatment sequences (BC or CB), according to a randomization scheme.

Treatment Sequence BC: On Day 1 (Period 1), a single oral dose of 300 mg of Compound A (4×75-mg tablets) is administered in the morning following a fast of at least 10 hours prior to and 4 hours after dosing (Treatment B). On Day 4 (Period 2), a single oral dose of 300 mg of Compound A (4×75-mg tablets) is administered in the morning approximately 30 minutes after starting a standard low-fat meal (Treatment C) at the same time of day (±1 hour) as the actual Day 1 Compound A dose.

Treatment Sequence CB: On Day 1 (Period 1), a single oral dose of 300 mg of Compound A (4×75-mg tablets) is administered in the morning approximately 30 minutes after starting a standard low-fat meal (Treatment C). On Day 4 (Period 2), a single oral dose of 300 mg of Compound A (4×75-mg tablets) is administered in the morning following a fast of at least 10 hours prior to and 4 hours after dosing (Treatment B) at the same time of day (±1 hour) as the actual Day 1 Compound A dose.

Group 3: pH-Effect Fasted Group (Tablet Formulation)

In Group 3, a single oral dose of Compound A is administered via tablets containing Compound A digentisate Form I under fasted conditions in Period 1. In Period 2, a single oral dose of Compound A via tablets containing Compound A digentisate Form I is coadministered under fasted conditions following multiple oral doses of esomeprazole.

Period 1 (Treatment B): a single oral dose of 300 mg of Compound A (4×75-mg tablets) is administered in the morning on Day 1 following a fast of at least 10 hours prior to and 4 hours after dosing.

Period 2 (Treatment D): a single oral dose of 40 mg esomeprazole (1×40-mg capsule) is administered QD in the morning on Days 4 through 8, following a fast of at least 8 hours prior to esomeprazole dosing, followed by a standard low-fat meal administered approximately 1 hour after dosing. On Day 9, subjects are administered a single oral dose of 40 mg esomeprazole (1×40-mg capsule) immediately followed by a single oral dose of 300 mg of Compound A (4×75-mg tablets) in the morning, following a fast of at least 10 hours prior to and 4 hours after esomeprazole and Compound A coadministration, at the same time of day (±1 hour) as the actual Day 1 Compound A dose.

Group 4: pH-Effect Fed Group (Tablet Formulation)

In Group 4, a single oral dose of Compound A is administered via tablets containing Compound A digentisate Form I under fed conditions in Period 1. In Period 2, a single oral dose of Compound A via tablets containing Compound A digentisate Form I is coadministered under fed conditions following multiple oral doses of esomeprazole.

Period 1 (Treatment C): a single oral dose of 300 mg of Compound A (4×75-mg tablets) is administered in the morning on Day 1 approximately 30 minutes after starting a standard low-fat meal.

Period 2 (Treatment E): a single oral dose of 40 mg esomeprazole (1×40-mg capsule) is administered QD in the morning on Days 4 through 8, following a fast of at least 8 hours prior to esomeprazole dosing, followed by a standard low-fat meal administered approximately 1 hour after dosing. On Day 9, subjects are administered a single oral dose of 40 mg esomeprazole immediately followed by a single oral dose of 300 mg Compound A (4×75-mg tablets) in the morning, approximately 30 minutes after starting a standard low-fat meal, at the same time of day (±1 hour) as the actual Day 1 Compound A dose.

There is a washout period of 3 days between the 2 doses of Compound A administered to subjects in Groups 1 and 2 and between the first dose of Compound A administered on Day 1 and the first dose of esomeprazole administered to subjects in Groups 3 and 4.

All study drugs are administered orally with approximately 240 mL of water. An additional 100 mL of water may be administered if needed.

Standard low-fat meals should be entirely consumed within 30 minutes. A standard low-fat meal is as follows: 400-500 total calories; 11-14 grams fat; 25% calories from fat.

Serial PK blood samples for the analysis of plasma concentrations of Compound A are collected from predose through 48 hours post-Compound A dose for each treatment period of each of the 4 treatment groups. In addition, urine is collected from predose through 24 hours postdose for Period 1 of Group 3 for the analysis of urine concentrations of Compound A. Samples collected for the analysis of plasma and urine concentrations of Compound A may be stored and analyzed for future exploratory analysis, such as quantification of metabolites of Compound A.

Whenever possible, the following PK parameters are calculated for each subject, based on the plasma concentrations of Compound A (as appropriate): AUC from hour 0 to 24 hours postdose, as calculated by the linear trapezoidal rule for increasing and decreasing concentrations (AUC0-24), AUC from hour 0 to 48 hours postdose, as calculated by the linear trapezoidal rule for increasing and decreasing concentrations (AUC0-48; if possible), AUC from hour 0 to the last measurable concentration, calculated using the linear trapezoidal rule for increasing and decreasing concentrations (AUC0-t), AUC from hour 0 extrapolated to infinity (AUC0-inf), percentage extrapolation for AUC0-inf (% AUCextrap), Cmax, time to Cmax (tmax), apparent terminal elimination rate constant ($\lambda Z$), apparent systemic clearance (CL/F), apparent plasma terminal elimination half-life (t½), and apparent volume of distribution at terminal phase (VZ/F). The $\lambda Z$ and t½ are calculated by linear least squares regression analysis using the maximum number of points in the terminal log-linear phase (e.g., 3 or more non-zero plasma concentrations). Individual subject measurements as well as summary statistics (e.g., group averages, standard deviations, coefficients of variation, ranges) are to be reported.

Whenever possible, the following PK parameters are calculated for each subject in Period 1 of Group 3, based on the urine concentrations of Compound A (as appropriate): amount of drug excreted in urine (Ae), percentage of dose excreted unchanged in urine (Fe), and renal clearance (CLR).

Capsule Formulation. A capsule containing crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one is prepared as follows. Neat crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one powder is filled into Size #0 light blue hypromellose capsule shells at 75 mg active strength per capsule.

Tablet Formulation. A tablet containing Compound A digentisate Form I is prepared as follows. Tablets are prepared by blending crystalline Compound A digentisate Form I with microcrystalline cellulose (MCC), mannitol, Poly(1-vinylpyrrolidone-co-Vinyl Acetate) (PVP VA), croscarmellose sodium, colloidal silica dioxide, and sodium stearyl fumarate. Following blending, the powder is dry granulated and milled to create free flowing granules. The granules are blended with croscarmellose sodium, talc, colloidal silica dioxide, and sodium stearyl fumarate to create the final blend. Tablets (containing 15, mg, 25 mg, 75 mg, or 150 mg active) are made from the final blend by compression. Finally, the tablets are cosmetically coated using a conventional pan coating procedure. See Table 10 below for tablet formulations.

TABLE 10

| | Component | % w/w | 15 mg (mg/tablet) | 25 mg (mg/tablet) | 75 mg* (mg/tablet) | 150 mg (mg/tablet) |
|---|---|---|---|---|---|---|
| Intra-Granular | Compound A digentisate Form I | 32.258 | 24.194 | 40.323 | 120.968 | 241.935 |
| | Microcrystalline Cellulose | 37.242 | 27.932 | 46.553 | 139.658 | 279.315 |
| | Mannitol Spray Processed | 15.000 | 11.250 | 18.750 | 56.250 | 112.500 |
| | PVP VA | 3.000 | 2.250 | 3.750 | 11.250 | 22.500 |
| | Croscarmellose Sodium (CCS) | 4.000 | 3.000 | 5.000 | 15.000 | 30.000 |
| | Colloidal Silica Dioxide | 0.250 | 0.188 | 0.313 | 0.938 | 1.875 |
| | Sodium Stearyl Fumarate (SSF) | 1.500 | 1.125 | 1.875 | 5.625 | 11.250 |
| | Sub Total | 93.250 | 69.938 | 116.563 | 349.688 | 699.375 |
| Extra-Granular | Croscarmellose Sodium (CCS) | 2.000 | 1.500 | 2.500 | 7.500 | 15.000 |
| | Talc | 2.000 | 1.500 | 2.500 | 7.500 | 15.000 |
| | Colloidal Silica Dioxide | 2.250 | 1.688 | 2.813 | 8.438 | 16.875 |
| | Sodium Stearyl Fumarate (SSF) | 0.500 | 0.375 | 0.625 | 1.875 | 3.750 |
| | Sub Total | 6.750 | 5.063 | 8.438 | 25.313 | 50.625 |
| Total Uncoated | | 100.0 | 75.00 | 125.0 | 375.0 | 750.0 |
| Coating System | Opadry QX Coating System | 3.000 | 2.250 | 3.750 | 11.250 | 22.500 |
| | Purified Water | Q.S. | Q.S. | Q.S. | Q.S. | Q.S. |
| Total Coated | | 103.0 | 77.3 | 128.75 | 386.25 | 772.500 |

*The 75 mg tablet formulation is used in the study

Study Results

Group 1: Tablet Versus Capsule Comparison Group (Fasted State)

Figure 6:
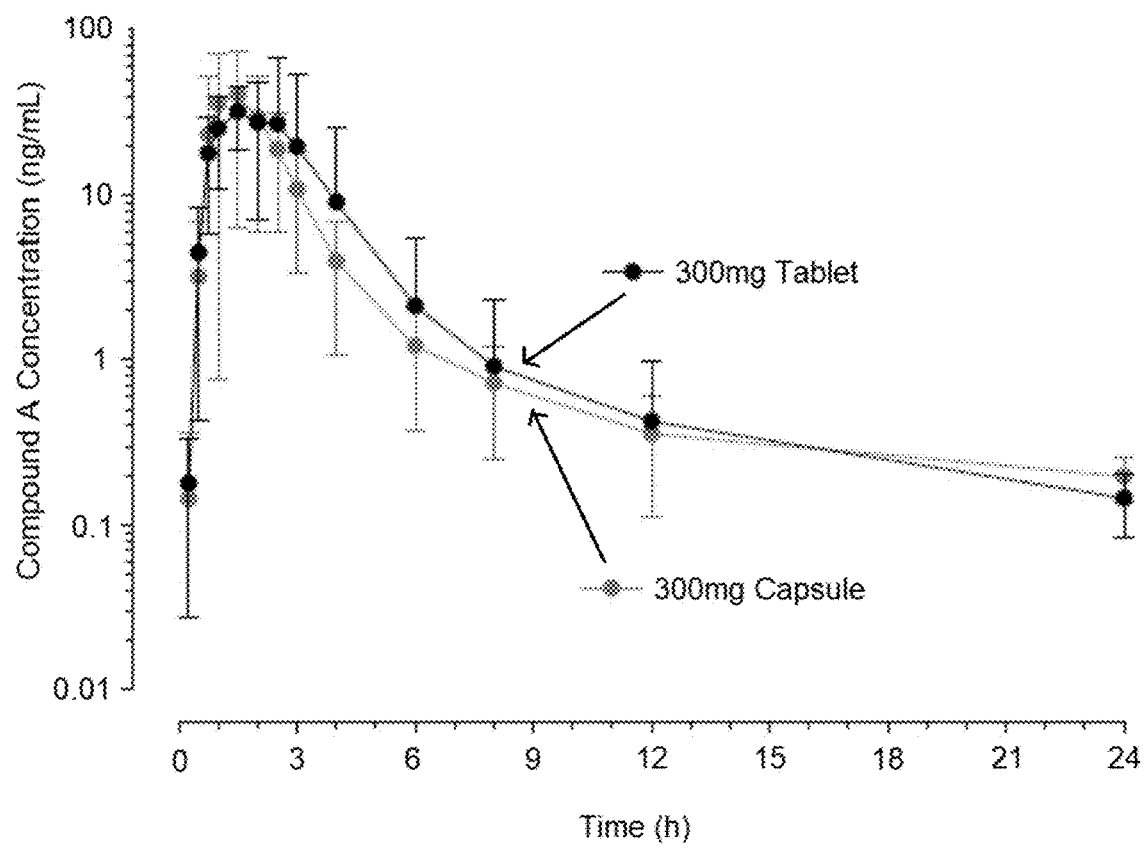
FIG. 6 shows mean observed plasma concentrations of Compound A (+/− standard deviation) over time when administered as Compound A crystalline free base (in a capsule) versus Compound A digentisate Form I (in a tablet formulation) in healthy adult subjects under fasted conditions.

As shown in Table 11 and FIG. 6, capsule and tablet formulations provide comparable relative bioavailability in healthy volunteers (n=14).

TABLE 11

Group 1 Preliminary Results
Matrix: Plasma; Analyte: Compound A

| Parameter | Treatment | n | GLSM | GMR (90% CI) | Within-subject CV |
|---|---|---|---|---|---|
| $AUC_{0-24}$ (h * ng/mL) | Capsule | 14 | 65.0 | 1.16 | 26.5 |
| | Tablet | 14 | 75.4 | (0.938, 1.44) | |
| $AUC_{0-t}$ (h * ng/mL) | Capsule | 14 | 64.8 | 1.15 | 26.4 |
| | Tablet | 14 | 74.7 | (0.932, 1.42) | |
| $AUC_{0-\infty}$ (h * ng/mL) | Capsule | 14 | 67.9 | 1.11 | 25.0 |
| | Tablet | 14 | 75.7 | (0.912, 1.36) | |
| $C_{max}$ (ng/mL) | Capsule | 14 | 34.9 | 1.02 | 31.4 |
| | Tablet | 14 | 35.7 | (0.795, 1.31) | |

CI = confidence interval;
CV = coefficient of variation (%);
GLSM = geometric least squares mean;
n = number of subjects with valid observations;
GMR = geometric mean ratio.
The GLSMs, ratios of GLSMs, and corresponding CIs were obtained by taking the exponential of the least square means (LSMs), differences in LSMs, and corresponding CIs on the natural log (ln) scale.

Group 2: Food-Effect Comparison Group (Tablet Formulation)

Figure 7:
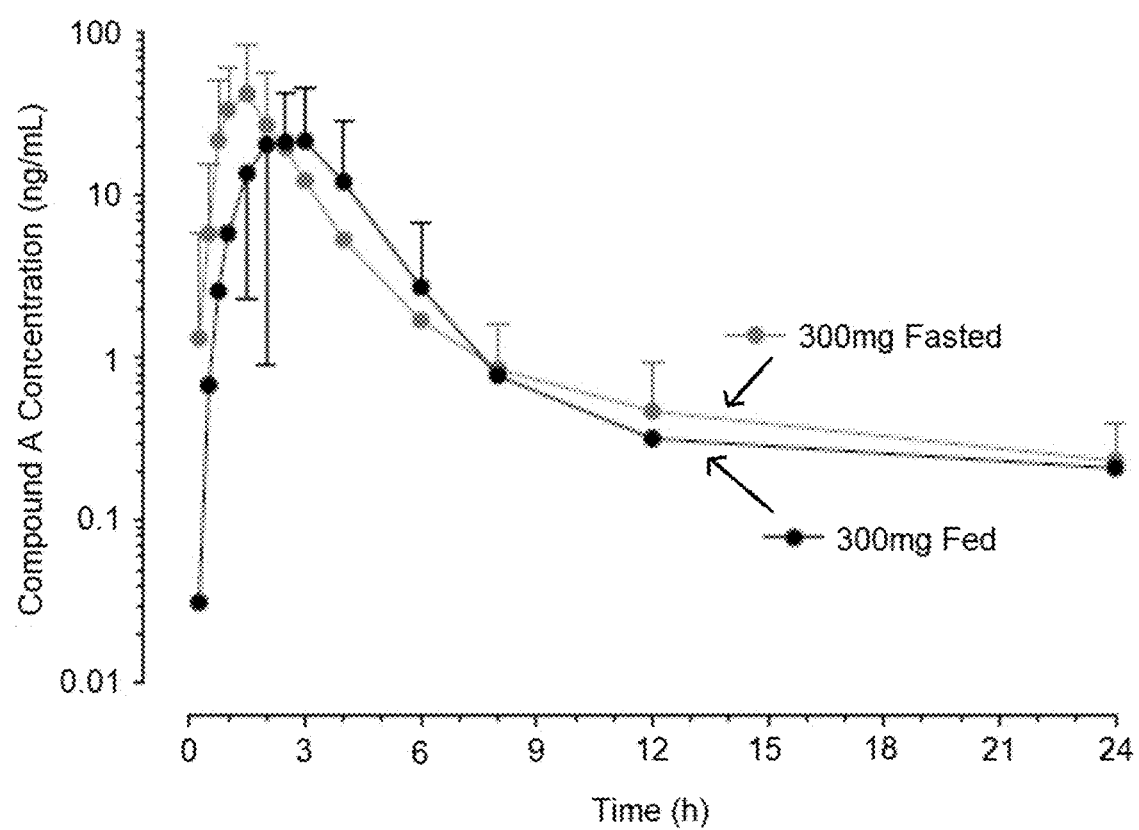
FIG. 7 shows mean observed plasma concentrations of Compound A (+/− standard deviation) over time when administered as Compound A digentisate Form I (in a tablet formulation) in healthy adult subjects under fasted versus fed conditions.

As shown in Table 12 and FIG. 7, the tablet formulation provides comparable relative bioavailability in healthy volunteers (n=14) under fed and fasted conditions.

TABLE 12

Group 2 Preliminary Results
Matrix: Plasma; Analyte: Compound A

| Parameter | Treatment | n | GLSM | GMR (90% CI) | Within-subject CV |
|---|---|---|---|---|---|
| $AUC_{0-24}$ (h * ng/mL) | Tablet (Fasted) | 14 | 53.9 | 0.906 | 23.4 |
| | Tablet (Fed) | 14 | 48.8 | (0.777, 1.06) | |
| $AUC_{0-t}$ (h * ng/mL) | Tablet (Fasted) | 14 | 53.5 | 0.901 | 23.7 |
| | Tablet (Fed) | 14 | 48.2 | (0.771, 1.05) | |
| $AUC_{0-\infty}$ (h * ng/mL) | Tablet (Fasted) | 14 | 55.3 | 0.882 | 23.1 |
| | Tablet (Fed) | 14 | 48.8 | (0.758, 1.03) | |
| $C_{max}$ (ng/mL) | Tablet (Fasted) | 14 | 29.5 | 0.688 | 36.7 |
| | Tablet (Fed) | 14 | 20.3 | (0.542, 0.872) | |

CI = confidence interval;
CV = coefficient of variation (%);
GLSM = geometric least squares mean;
n = number of subjects with valid observations;
GMR = geometric mean ratio.
The GLSMs, ratios of GLSMs, and corresponding CIs were obtained by taking the exponential of the least square means (LSMs), differences in LSMs, and corresponding CIs on the natural log (ln) scale.

Group 3: pH-Effect Fasted Group (Tablet Formulation)

Figure 8:
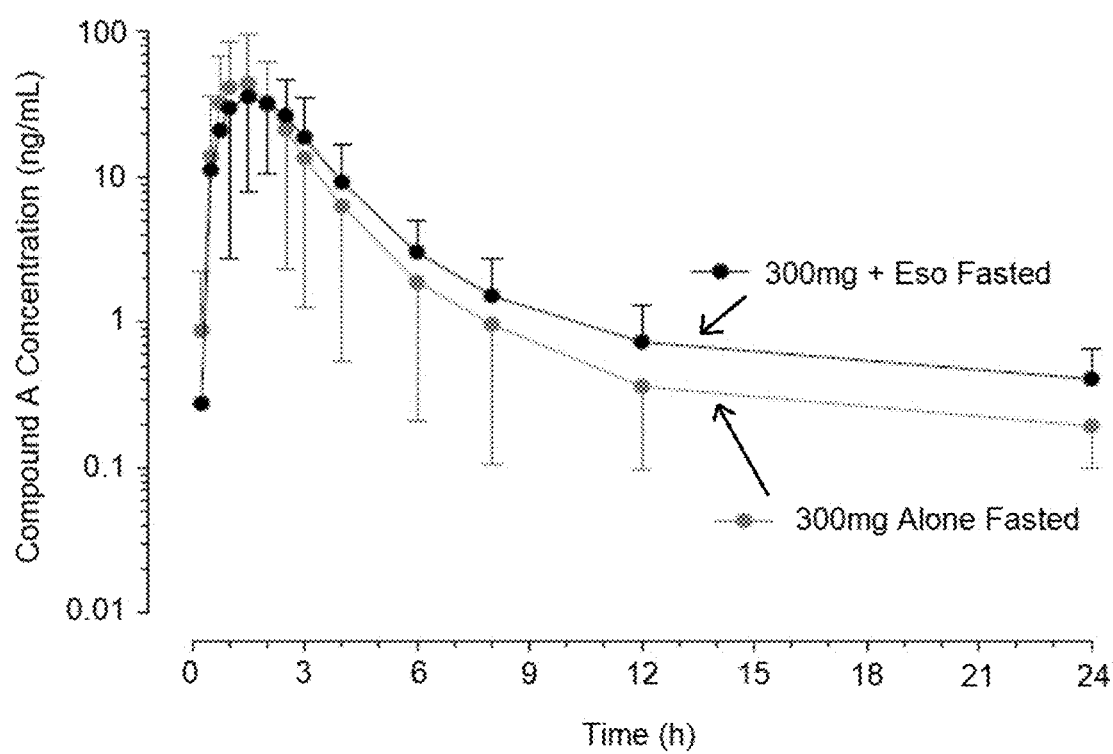
FIG. 8 shows mean observed plasma concentrations of Compound A (+/− standard deviation) over time when administered as Compound A digentisate Form I (in a tablet formulation) in healthy adult subjects under fasted conditions and following multiple oral doses of esomeprazole.

As shown in Table 13 and FIG. 8, the tablet formulation alone and with esomeprazole (PPI) provides comparable relative bioavailability in healthy volunteers (n=14) under fasted conditions.

TABLE 13

Group 3 Preliminary Results
Matrix: Plasma; Analyte: Compound A

| Parameter | Treatment | n | GLSM | GMR (90% CI) | Within-subject CV |
|---|---|---|---|---|---|
| $AUC_{0-24}$ (h * ng/mL) | Tablet | 14 | 78.4 | 1.20 | 27.2 |
| | Tablet + Eso | 14 | 94.2 | (0.966, 1.49) | |
| $AUC_{0-t}$ (h * ng/mL) | Tablet | 14 | 77.9 | 1.21 | 25.6 |
| | Tablet + Eso | 14 | 94.0 | (0.982, 1.48) | |
| $AUC_{0-\infty}$ (h * ng/mL) | Tablet | 14 | 79.2 | 1.22 | 26.2 |
| | Tablet + Eso | 14 | 96.2 | (0.985, 1.50) | |
| $C_{max}$ (ng/mL) | Tablet | 14 | 42.2 | 1.03 | 33.5 |
| | Tablet + Eso | 14 | 43.5 | (0.790, 1.34) | |

CI = confidence interval;
CV = coefficient of variation (%);
GLSM = geometric least squares mean;
n = number of subjects with valid observations;
GMR = geometric mean ratio.
The GLSMs, ratios of GLSMs, and corresponding CIs were obtained by taking the exponential of the least square means (LSMs), differences in LSMs, and corresponding CIs on the natural log (ln) scale.

Group 4: pH-Effect Fed Group (Tablet Formulation)

Figure 9:
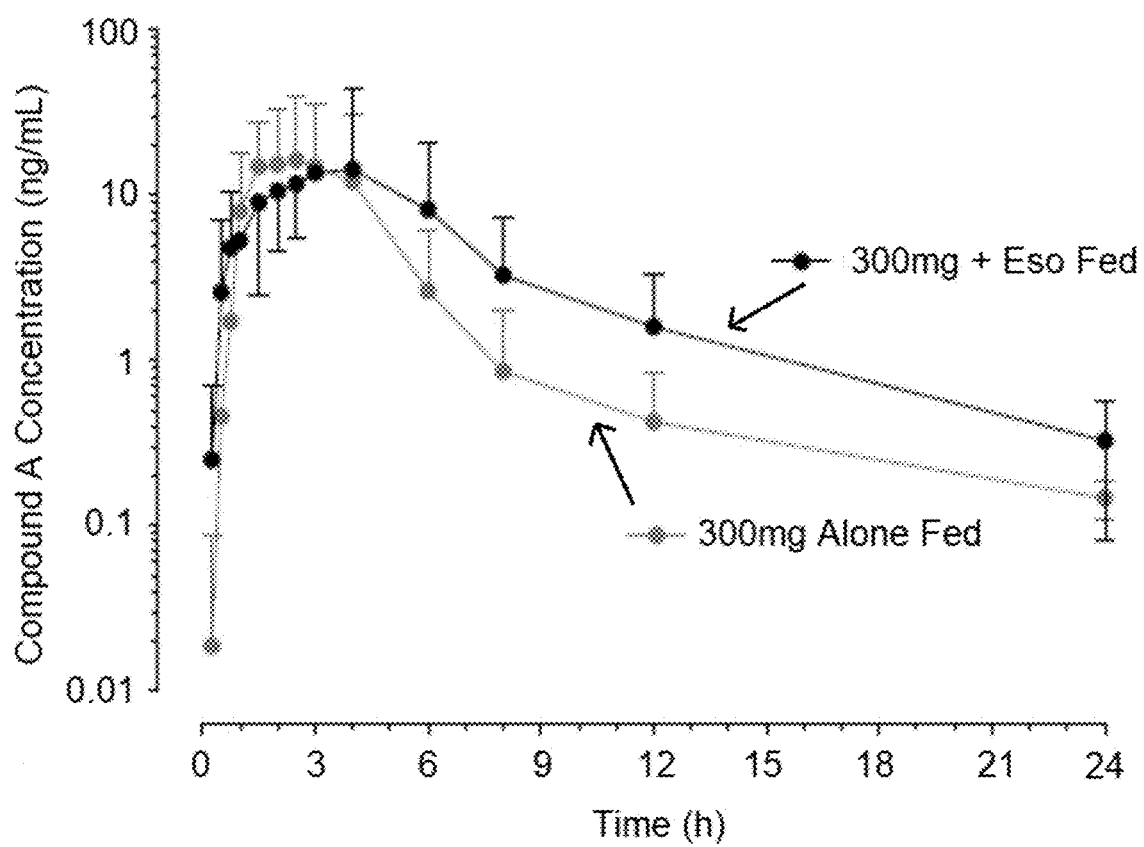
FIG. 9 shows mean observed plasma concentrations of Compound A (+/− standard deviation) over time when administered as Compound A digentisate Form I (in a tablet formulation) in healthy adult subjects under fed conditions and following multiple oral doses of esomeprazole.

As shown in Table 14 and FIG. 9, the tablet formulation alone and with esomeprazole (PPI) provides comparable relative bioavailability in healthy volunteers (n=14) under fed conditions.

TABLE 14

Group 4 Preliminary Results
Matrix: Plasma; Analyte: Compound A

| Parameter | Treatment | n | GLSM | GMR (90% CI) | Within-subject CV |
|---|---|---|---|---|---|
| $AUC_{0-24}$ (h * ng/mL) | Tablet | 14 | 49.9 | 1.28 | 23.3 |
| | Tablet + Eso | 13 | 63.7 | (1.09, 1.50) | |
| $AUC_{0-t}$ (h * ng/mL) | Tablet | 14 | 49.4 | 1.28 | 23.4 |
| | Tablet + Eso | 13 | 63.2 | (1.09, 1.50) | |
| $AUC_{0-\infty}$ (h * ng/mL) | Tablet | 14 | 50.0 | 1.30 | 23.8 |
| | Tablet + Eso | 12 | 65.1 | (1.10, 1.54) | |
| $C_{max}$ (ng/mL) | Tablet | 14 | 24.9 | 0.597 | 45.3 |
| | Tablet + Eso | 13 | 14.8 | (0.442, 0.807) | |

CI = confidence interval;
CV = coefficient of variation (%);
GLSM = geometric least squares mean;
n = number of subjects with valid observations;
GMR = geometric mean ratio.
The GLSMs, ratios of GLSMs, and corresponding CIs were obtained by taking the exponential of the least square means (LSMs), differences in LSMs, and corresponding CIs on the natural log (ln) scale.

Study Conclusions

Food Effect. Data from healthy volunteers given Compound A digentisate Form I in a tablet formulation with a low-fat meal shows no effect of food on Compound A exposure. Hence, Compound A digentisate Form I in a tablet formulation can be given with or without a meal.

pH Effect. Data from healthy volunteers given Compound A digentisate Form I in a tablet formulation in a fasted or fed state shows no effect of proton pump inhibitor (PPI) on Compound A exposure. Hence, Compound A digentisate Form I in a tablet formulation can be given with or without PPIs and antacids in the fasted or fed state.

We claim:

1. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

2. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), characterized by at least one of:
   (i) an X-ray powder diffraction pattern using CuKa radiation having at least one peak at diffraction angle 2-theta of 7.2°±0.2°, 9.0°±0.2°, 9.5°±0.2°, 10.9°±0.2°, 11.7°±0.2°, 14.5°±0.2°, 15.7°±0.2°, 16.8°±0.2°, 17.2°±0.2°, 19.2°±0.2°, 20.8°±0.2°, 24.1°±0.2°, 24.7°±0.2°, or 25.8°±0.2°; or
   (ii) a $^{13}C$ solid state NMR (100.6 MHz) spectrum which comprises at least one peak referenced to the high-field resonance of adamantane (d=29.5 ppm) at: 5.1, 5.9, 8.2, 12.8, 23.9, 32.1, 39.0, 41.9, 44.1, 49.6, 52.7, 63.1, 68.1, 102.7, 114.0, 115.9, 117.6, 118.0, 119.0, 119.3, 120.1, 122.4, 126.7, 127.1, 127.6, 128.4, 129.2, 130.3, 133.9, 141.0, 145.2, 149.4, 150.8, 153.0, 155.1, 159.8, 166.3, 174.2, or 175.2 ppm (±0.2 ppm, respectively).

3. The solid form of claim 2, characterized by an X-ray powder diffraction pattern using CuKa radiation having a peak at diffraction angle 2-theta of 9.0°±0.2° in combination with at least one peak selected from 7.2°±0.2°, 9.5°±0.2°, and 11.7°±0.2°.

4. The solid form of claim 2, characterized by a $^{13}C$ solid state NMR (100.6 MHz) spectrum which comprises peaks referenced to the high-field resonance of adamantane (d=29.5 ppm) at: 12.8, 23.9, 41.9, 68.1, 149.4, and 155.1 ppm (±0.2 ppm, respectively).

5. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), characterized by an X-ray powder diffraction pattern using CuKa radiation having at least one peak at diffraction angle 2-theta of 4.9°±0.2°, 6.5°±0.2°, 7.5°±0.2°, 8.2°±0.2°, 9.9°±0.2°, 12.0°±0.2°, 12.7°±0.2°, 14.8°±0.2°, 15.0°±0.2°, 15.4°±0.2°, 16.0°±0.2°, 17.0°±0.2°, 17.4°±0.2°, or 19.6°±0.20.

6. The solid form of claim 5, characterized by an X-ray powder diffraction pattern using CuKa radiation having a peak at diffraction angle 2-theta of 6.5° in combination with at least one peak selected from 4.9°, 8.2°, and 12.7° (±0.2°, respectively).

7. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2), characterized by an X-ray powder diffraction pattern using CuKa radiation having at least one peak at diffraction angle 2-theta of 5.5°±0.2°, 8.5°±0.2°, 11.0°±0.2°, 11.9°±0.2°, 12.4°±0.2°, 14.0°±0.2°, 14.3°±0.2°, 16.3°±0.2°, 16.6°±0.2°, 17.0°±0.2°, or 19.1°±0.2°.

8. The solid form of claim 7, characterized by an X-ray powder diffraction pattern using CuKa radiation having a peak at diffraction angle 2-theta of 5.5°±0.2°in combination with at least one peak selected from 8.5°±0.2°, 11.0°±0.2°, and 11.9°±0.2°.

9. A solid form that is amorphous 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,5-dihydroxybenzoic acid (1:2).

10. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,4-dihydroxybenzoic acid (1:2).

11. A solid form that is crystalline 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, 2,3-dihydroxybenzoic acid (1:2).

12. The solid form of claim 11, characterized by an X-ray powder diffraction (XRPD) pattern using CuKa radiation having a peak at diffraction angle 2-theta of 11.5°±0.2° in combination with at least one peak selected from 8.9°±0.2°, 15.0°±0.2°, and 24.6°±0.2°.

13. A pharmaceutical composition comprising a solid form of claim 1, and a pharmaceutically acceptable carrier, diluent, or excipient.

14. A method of treating a cancer in a patient expressing an IDH mutation, comprising administering to a patient in need thereof a therapeutically effective amount of a solid form of claim 1.

15. The method of claim 14, wherein the IDH mutation is an IDH1 mutation.

16. The method of claim 15, wherein the IDH1 mutation is an IDH1 R132 mutation.

17. The method of claim 14, wherein the IDH mutation is an IDH2 mutation.

18. The method of claim 17, wherein the IDH2 mutation is an IDH2 R140 mutation.

19. The method of claim 17, wherein the IDH2 mutation is an IDH2 R172 mutation.

20. The method of claim 14, wherein the cancer is a solid tumor cancer.

21. The method of claim 20, wherein the solid tumor cancer is cholangiocarcinoma, head and neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma.

22. The method of claim 20, wherein the solid tumor cancer is cholangiocarcinoma.

23. The method of claim 14, wherein the cancer is a hematologic malignancy.

24. The method of claim 23, wherein the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia.

25. The method of claim 23, wherein the hematologic malignancy is acute myeloid leukemia.

* * * * *